US012734369B2

(12) United States Patent
Chon et al.

(10) Patent No.: US 12,734,369 B2
(45) Date of Patent: Sep. 15, 2026

(54) CARDIOPULMONARY RESUSCITATION, TREATMENT, AND ANALYSIS

(71) Applicant: University of Connecticut, Farmington, CT (US)

(72) Inventors: Ki Chon, Portsmouth, RI (US); Mahdi Pirayesh Shirazi Nejad, Coventry, FL (US)

(73) Assignee: THE UNIVERSITY OF CONNECTICUT, Farmington, CT (US)

( * ) Notice: Subject to any disclaimer, the term of this patent is extended or adjusted under 35 U.S.C. 154(b) by 294 days.

(21) Appl. No.: 18/659,762

(22) Filed: May 9, 2024

(65) Prior Publication Data

US 2024/0342496 A1 Oct. 17, 2024

Related U.S. Application Data

(63) Continuation-in-part of application No. PCT/US2022/048428, filed on Oct. 31, 2022.
(Continued)

(51) Int. Cl.
*A61N 1/39* (2006.01)
*A61B 5/00* (2006.01)
(Continued)

(52) U.S. Cl.
CPC .............. *A61N 1/395* (2013.01); *A61B 5/361* (2021.01); *A61B 5/7207* (2013.01);
(Continued)

(58) Field of Classification Search
CPC .... A61N 1/395; A61N 1/39044; A61B 5/361; A61B 5/7207; A61B 5/4836;
(Continued)

(56) References Cited

U.S. PATENT DOCUMENTS

2011/0105930 A1 5/2011 Thiagarajan et al.
2016/0360977 A1 12/2016 Salehizadeh et al.
(Continued)

FOREIGN PATENT DOCUMENTS

WO 2023086233 A1 5/2023

OTHER PUBLICATIONS

Jekova, Irena, and Vessela Krasteva. "Optimization of end-to-end convolutional neural networks for analysis of out-of-hospital cardiac arrest rhythms during cardiopulmonary resuscitation." Sensors, vol. 21, No. 12, Jun. 15, 2021, p. 4105, https://doi.org/10.3390/s21124105. (Year: 2021).*
(Continued)

*Primary Examiner* — Paula J Stice
(74) *Attorney, Agent, or Firm* — CANTOR COLBURN LLP

(57) ABSTRACT

An apparatus for treating a person having cardiac arrest includes a processor and a lead in communication with the processor, the lead being configured to receive a segment of electrocardiogram (ECG) data from the person while undergoing cardiopulmonary resuscitation (CPR). The apparatus also includes a non-transitory computer-readable medium having: a first Convolutional Neural Network-based Encoder-Decoder (CNNED) structure to reduce artifacts due to the CPR; a second CNNED structure cascaded with the first CNNED structure to further reduce artifacts; and instructions to determine a first arrhythmia classification using the first CNNED structure, determine a second arrhythmia classification using the second CNNED structure in response to the first arrhythmia classification indicating a shockable arrhythmia event; and transmit a signal to apply a defibrillation shock to the person in response to the first arrhythmia classification and the second arrhythmia classification indicating a shockable arrhythmia of the person.

20 Claims, 13 Drawing Sheets

Related U.S. Application Data

(60) Provisional application No. 63/298,824, filed on Jan. 12, 2022, provisional application No. 63/277,392, filed on Nov. 9, 2021.

(51) Int. Cl.

| | |
|---|---|
| ***A61B 5/361*** | (2021.01) |
| ***A61H 31/00*** | (2006.01) |
| ***G06N 3/045*** | (2023.01) |
| ***G06N 3/0464*** | (2023.01) |

(52) U.S. Cl.
CPC ......... *A61H 31/005* (2013.01); *A61N 1/3987* (2013.01); *G06N 3/045* (2023.01); *G06N 3/0464* (2023.01); *A61H 2230/045* (2013.01)

(58) Field of Classification Search
CPC .... A61B 5/7217; A61B 5/7257; G06N 3/045; G06N 3/0464; A61H 2230/045
See application file for complete search history.

(56) References Cited

U.S. PATENT DOCUMENTS

| | | | | |
|---|---|---|---|---|
| 2016/0361021 | A1 | 12/2016 | Salehizadeh et al. | |
| 2020/0085333 | A1 * | 3/2020 | Freed .................... | G06N 3/084 |

OTHER PUBLICATIONS

Isasi, Iraia, et al. “Rhythm analysis during cardiopulmonary resuscitation using convolutional neural networks.” Entropy, vol. 22, No. 6, May 27, 2020, p. 595, https://doi.org/10.3390/e22060595. (Year: 2020).*

International Search Report and Written Opinion; PCT/US2022/048428; United States Patent Office; Mailed Feb. 28, 2023; 15 pages.

* cited by examiner

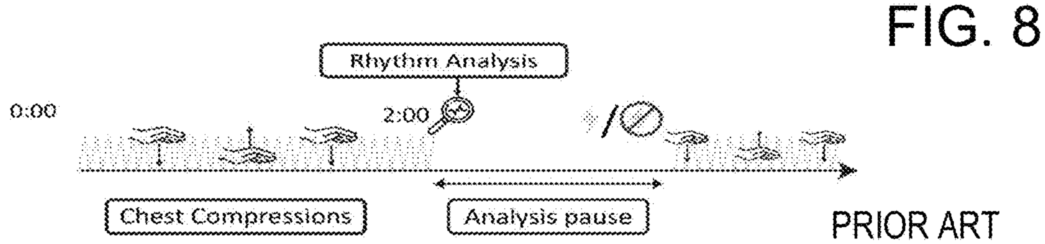
FIG. 8
PRIOR ART
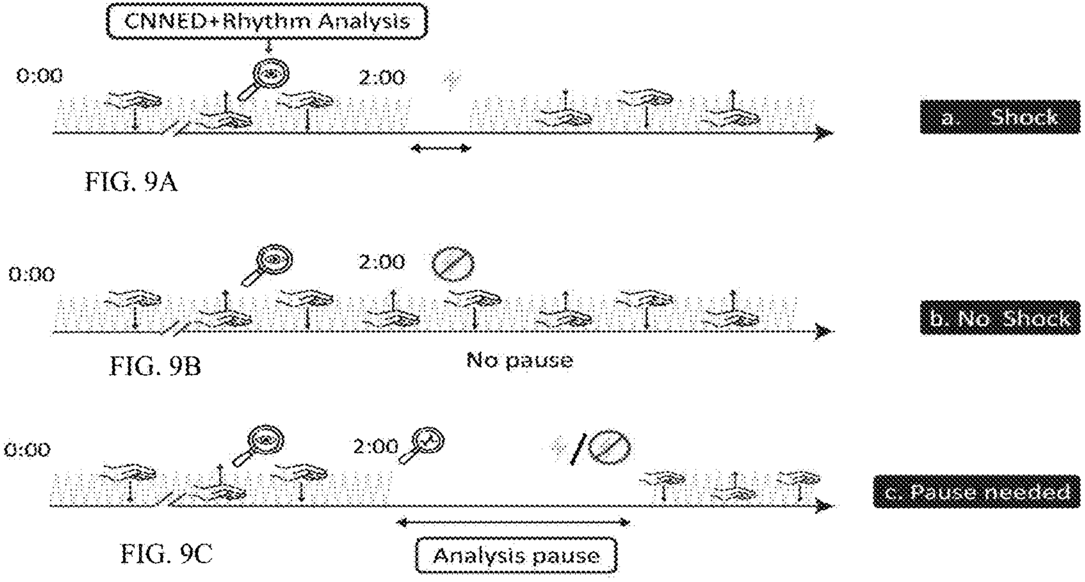
FIG. 9A
FIG. 9B
FIG. 9C

CARDIOPULMONARY RESUSCITATION, TREATMENT, AND ANALYSIS

CROSS REFERENCE TO RELATED APPLICATIONS

This application is a continuation-in-part of International Application No. PCT/US2022/048428 filed Oct. 31, 2022. International Application No. PCT/US2022/048428 filed Oct. 31, 2022, claims the benefit of U.S. Provisional Application No. 63/277,392 filed Nov. 9, 2021, and U.S. Provisional Application No. 63/298,824 filed Jan. 12, 2022, all of which are incorporated herein in their entirety.

BACKGROUND

Since its advent, cardiopulmonary resuscitation (CPR) has saved countless lives. CPR can be used to mimic the pumping motion of the heart to keep blood flowing through the body. CPR may be used during ventricular fibrillation where sudden cardiac death may occur, providing an opportunity for CPR to prolong life until an external defibrillator is available. In order to ensure proper application of the external defibrillator, an electrocardiogram may provide insight into heart operation. During an electrocardiogram analysis period, CPR may be interrupted to reduce motion artifacts in the electrocardiogram (ECG) signal, further reducing blood flow for oxygen-deprived organs.

The importance of CPR during SCA cannot be overstated. Its primary goal is to restore blood circulation and prevent brain damage by delivering oxygen to the brain and other vital organs. The brain, in particular, is highly sensitive to oxygen deprivation, and even a brief interruption in blood flow can lead to irreversible neurological damage. Therefore, CPR is a critical link in the chain of survival, a sequence of interconnected actions that, when executed swiftly, can significantly enhance the chances of survival from cardiac arrest. However, current automated external defibrillators (AEDs) need 8-20 seconds of CPR interruptions for reliable analysis and to decide when to defibrillate and apply the shock.

Unfortunately, a delay in electrical shock and CPR during shockable cardiac arrhythmias, like ventricular fibrillation (VF), results in a decrease of 10%-12% in survival probability per minute. However, if CPR is continuously performed, the decrease in survival rate is only 3%-4% per minute of delayed electrical shock. It is a significant improvement to accurately detect a shockable rhythm during CPR and enable earlier delivery of the shock, eliminating both the need for a full two-minute cycle of CPR and the need for CPR interruptions. Therefore, the development of a reliable shock advisory system capable of recognizing and removing CPR artifacts in ECG waveforms in near real-time holds a significant value.

SUMMARY

Methods, apparatuses, and systems are described for improving cardiopulmonary treatment and other technological fields. For a better understanding of the underlying concepts, there follows specific non-limiting examples:

Disclosed is an apparatus configured to treat fibrillation. For example, the apparatus shocks the patient to correct fibrillation (e.g., defibrillation). The apparatus includes one or more of circuitry, instructions, and other implements to determine whether a shock can treat the fibrillation and whether the patient is experiencing fibrillation based on an ECG signal. CPR artifacts imparted into the ECG signal can disrupt such determinations. A network of one or more of circuitry, instructions, and processing is disclosed to specifically remove CPR artifacts to avoid reducing blood flow for oxygen-deprived organs.

For example, an encoder-decoder network is disclosed to remove such CPR-related artifacts. The encoder-decoder network may be trained on ECG signals that include CPR-related artifacts and ECG signals that do not or have a reduced quantity of artifacts (e.g., clean ECG signals). As such, the network may be trained to receive an ECG signal with CPR-related artifacts and output a clean ECG signal without the artifacts. The network may also be trained to recognize shockable and non-shockable patients for treating the patient showing signs of fibrillation or other cardiopulmonary disorders. These and other techniques are described herein.

Also disclosed is an apparatus for treating a person having cardiac arrest. The apparatus includes a processor, a lead in communication with the processor, wherein the lead is configured to receive a first segment of electrocardiogram (ECG) data from the person when the person is undergoing cardiopulmonary resuscitation (CPR), and a non-transitory computer-readable medium. The non-transitory computer-readable medium includes a first Convolutional Neural Network-based Encoder-Decoder (CNNED) structure to reduce artifacts due to the CPR and a second CNNED structure cascaded with the first CNNED structure to further reduce artifacts due to the CPR. The non-transitory computer-readable medium also includes first instructions operable upon execution by the processor to (i) determine a first arrhythmia classification using the first CNNED structure, (ii) determine a second arrhythmia classification using the second CNNED structure in response to the first arrhythmia classification indicating a shockable arrhythmia event of the person, and (iii) transmit a signal to apply a defibrillation shock to the person in response to the first arrhythmia classification and the second arrhythmia classification indicating a shockable arrhythmia of the person.

Further disclosed is a non-transitory computer-readable medium associated with treating a person having cardiac arrest. The non-transitory computer-readable medium includes instructions operable upon execution by a processor to receive a first segment of electrocardiogram (ECG) data from the person when the person is undergoing cardiopulmonary resuscitation (CPR). The non-transitory computer-readable medium also includes a first Convolutional Neural Network-based Encoder-Decoder (CNNED) structure trained with a first combination of shockable arrhythmia events and non-shockable arrhythmia events to reduce artifacts due to the CPR and a second CNNED structure cascaded with the first CNNED structure and trained with a second combination of shockable arrhythmia events and non-shockable arrhythmia events wherein a number of the shockable arrhythmia events is greater than a number of non-shockable arrhythmia events in the second combination to further reduce artifacts due to the CPR. The non-transitory computer-readable medium further include instructions operable upon execution by the processor to determine a first arrhythmia classification using the first CNNED structure, determine a second arrhythmia classification using the second CNNED structure in response to the first arrhythmia classification indicating a shockable arrhythmia event of the person and transmit a signal to apply a defibrillation shock to the person in response to the first arrhythmia classification and the second arrhythmia classification indicating a shockable arrhythmia of the person.

Further disclosed is an automated external defibrillator (AED). The AED includes a processor, a lead associated with the processor, wherein the lead is configured to receive a first segment of electrocardiogram (ECG) data from a person, the person undergoing cardiopulmonary resuscitation (CPR), and a non-transitory computer-readable medium having machine executable instructions for implementing a method. The method includes a first Convolutional Neural Network-based Encoder-Decoder (CNNED) structure trained with a first combination of shockable arrhythmia events and non-shockable arrhythmia events to reduce artifacts due to the CPR, a second CNNED structure cascaded with the first CNNED structure and trained with a second combination of shockable arrhythmia events and non-shockable arrhythmia events wherein a number of the shockable arrhythmia events is greater than a number of non-shockable arrhythmia events in the second combination to further reduce artifacts due to the CPR, and a third CNNED structure cascaded with the first CNNED structure and trained with a third combination of shockable arrhythmia events and non-shockable arrhythmia events wherein a number of the shockable arrhythmia events is less than a number of non-shockable arrhythmia events in the third combination to further reduce artifacts due to the CPR. The non-transitory computer-readable medium also includes first instructions operable upon execution by the processor to (i) determine a first arrhythmia classification using the first CNNED structure, (ii) determine a second arrhythmia classification using the second CNNED structure in response to the first arrhythmia classification indicating a shockable arrhythmia event of the person; and (iii) apply a defibrillation shock to the person in response to the first arrhythmia classification and the second arrhythmia classification indicating a shockable arrhythmia of the person; second instructions operable upon execution by the processor to (iv) determine the second arrhythmia classification using the third CNNED structure in response to the first arrhythmia classification indicating a non-shockable arrhythmia event of the person; and (v) not apply the defibrillation shock to the person in response to the first arrhythmia classification and the second arrhythmia classification indicating a non-shockable arrhythmia of the person; third instructions operable upon execution by the processor to receive a second segment of the ECG data from the lead and implement the first instructions and the second instructions using the second segment in response to the first arrhythmia classification and the second arrhythmia classification not being in agreement, and fourth instructions operable upon execution by the processor to stop the CPR for a selected time period, receive a post-CPR segment of the ECG data, restart the CPR, and implement the first instructions and the second instructions using the post-CPR segment in response to the first arrhythmia classification and the second arrhythmia classification not being in agreement for a selected number of segments of the ECG data. The AED also includes a shock application device coupled to the lead and to the processor and configured to apply the defibrillation shock through the lead to the person in response to receiving a signal from the processor to apply the shock and a display coupled to the processor and configured to display a first indication that a defibrillation shock will not be applied to the person and a second indication informing that the CPR should be temporarily stopped for a selected period of time to obtain a clean segment of ECG data.

BRIEF DESCRIPTION OF THE DRAWINGS

In order to provide a better understanding techniques described herein, the figures provide non-limiting examples in accordance with one or more implementations of the present disclosure, in which:

FIG. 8 illustrates a prior art treatment for cardiac arrest;

FIGS. 9A, 9B, and 9C, collectively referred to as FIG. 9, depict aspects of a novel treatment for cardiac arrest using a Convolutional Neural Network-based Encoder-Decoder (CNNED) structure;

DETAILED DESCRIPTION

Figure 1:
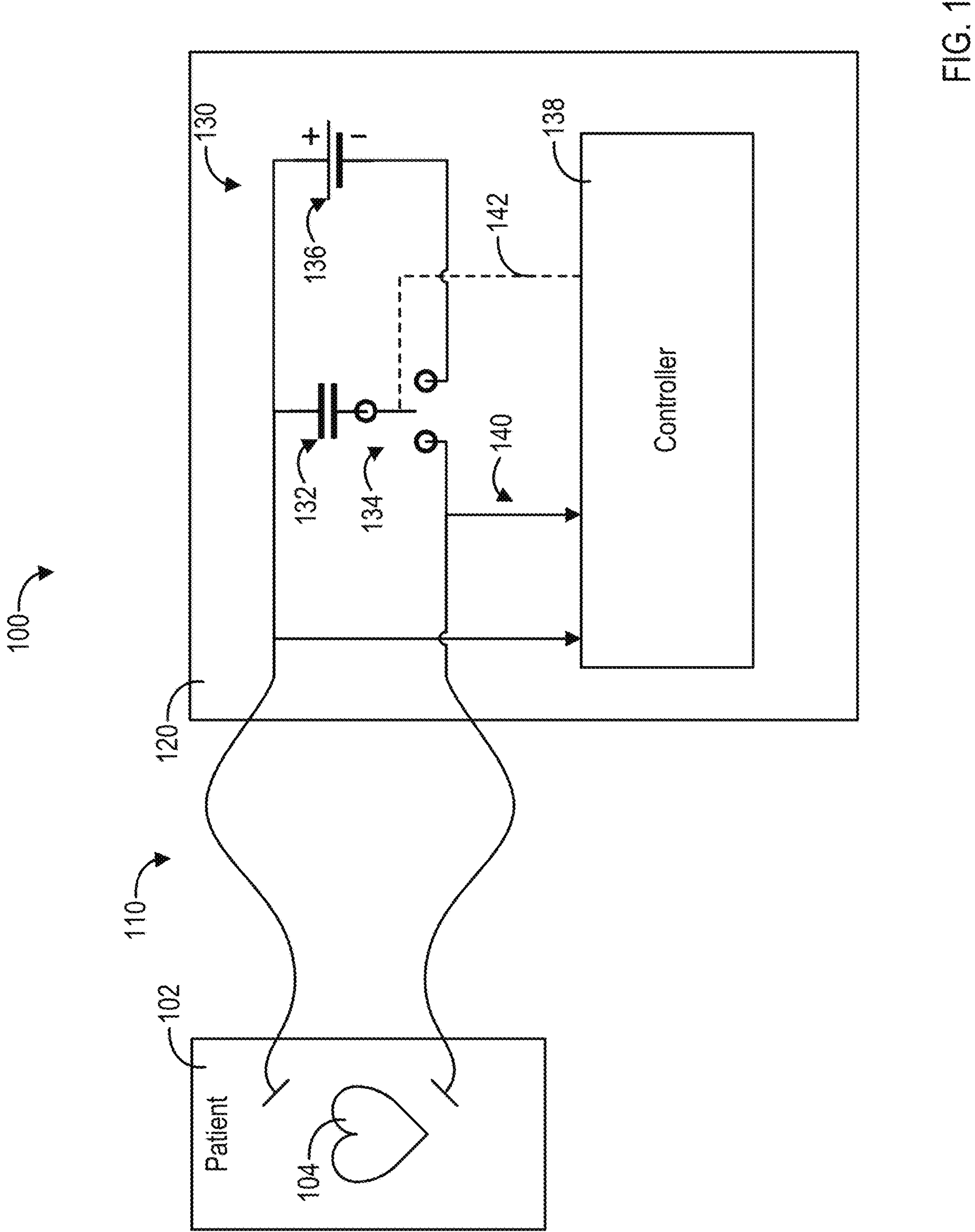
FIG. 1 illustrates an example system for treating a patient with cardiopulmonary issues in accordance with one or more implementations of the present disclosure.

It is understood that when combinations, subsets, interactions, groups, etc. of components are described that, while specific reference of each various individual and collective combinations and permutations of these may not be explicitly described, each is specifically contemplated and described herein. This applies to all parts of this disclosure including, but not limited to, steps in described methods. Thus, if there are a variety of additional steps that may be performed it is understood that each of these additional steps may be performed with any specific configuration or combination of configurations of the described methods.

As will be appreciated by one skilled in the art, hardware, software, or a combination of software and hardware may be implemented. Furthermore, a computer program product may be stored on a computer-readable storage medium (i.e., non-transitory) having processor-executable instructions (e.g., computer software) embodied in the storage medium. Any suitable computer-readable storage medium may be utilized including hard disks, CD-ROMs, optical storage devices, magnetic storage devices, memresistors, Non-Volatile Random Access Memory (NVRAM), flash memory, or a combination thereof.

Throughout this disclosure reference is made to block diagrams and flowcharts. It will be understood that each block of the block diagrams and flowcharts, and combinations of blocks in the block diagrams and flowcharts, respectively, may be implemented by processor-executable instructions. These processor-executable instructions may be loaded onto a special purpose computer or other programmable data processing instrument to produce a machine, such that the processor-executable instructions which execute on the computer or other programmable data processing instrument create a device for implementing the functions specified in the flowchart block or blocks.

These processor-executable instructions may also be stored in a computer-readable memory or a computer-readable medium (i.e., a non-transitory computer-readable medium) that may direct a computer or other programmable data processing instrument to function in a particular manner, such that the processor-executable instructions stored in the computer-readable memory produce an article of manufacture including processor-executable instructions for implementing the function specified in the flowchart block or blocks. The processor-executable instructions may also be loaded onto a computer or other programmable data processing instrument to cause a series of operational steps to be performed on the computer or other programmable instrument to produce a computer-implemented process such that the processor-executable instructions that execute on the computer or other programmable instrument provide steps for implementing the functions specified in the flowchart block or blocks.

Blocks of the block diagrams and flowcharts support combinations of devices for performing the specified functions, combinations of steps for performing the specified functions, and program instruction means for performing the specified functions. It will also be understood that each block of the block diagrams and flowcharts, and combinations of blocks in the block diagrams and flowcharts, may be implemented by special purpose hardware-based computer systems that perform the specified functions or steps, or combinations of special purpose hardware and computer instructions.

Methods and systems are described for using a machine learning classifier(s) for detection and classification. Machine learning (ML) is a subfield of computer science that gives computers the ability to learn through training without being explicitly programmed. Machine learning methods include, but are not limited to, deep-learning techniques, naïve Bayes classifiers, support vector machines, decision trees, neural networks, and the like.

The method steps recited throughout this disclosure may be combined, omitted, rearranged, or otherwise reorganized with any of the figures presented herein and are not intended to be limited to the four corners of each sheet presented.

Survival from out-of-hospital cardiac arrests (OHCA) depends on an accurate defibrillatory shock decision for a patient while, at the same time, the patient is in the process of receiving CPR. Since chest compressions induce severe artifacts (e.g., motion artifacts) in the electrocardiogram (ECG) signal, automatic external defibrillators require interruption of the provision of CPR to the patient during the rhythm analysis period. In many instances, the rhythm analysis period is eight seconds or greater. However, performing continuous CPR on the patient or CPR with interruptions less than the rhythm analysis period of eight seconds dramatically increases the chance of patient survival. Suppression of artifacts caused by CPR on the patient in near real-time using ECG data is disclosed in one or more of the implementations discussed herein. A network (e.g., a convolutional neural network having an encoder-decoder architecture) may use the ECG data, images of the ECG data, conversions of data using spectral analysis, or combinations thereof to train the network to learn distinct features that are representative of both the ECG signal and CPR artifacts. The network may include skip connections or symmetric skip connections to improve artifact reduction, and the decoder may take the results from the encoder and reconstruct what is perceived as an ECG with reduced motion artifacts that are imparted by providing CPR to the patient, allowing treatment of the patient without interruption or reduced interruption. The network may be trained using many different arrhythmias ECG signals, ECG data, images of the ECG data, conversions of that data using spectral analysis, or combinations thereof contaminated with CPR artifacts. The network may be further trained using uncontaminated ECG data or those determined when CPR artifacts are not present to ensure uncontaminated ECG data is not needlessly adjusted.

Sudden cardiac arrest (SCA) is caused by a loss of heart function that occurs rapidly and most often outside of the hospital. It is the largest determinant of natural death in the United States, killing more than 325,000 adults each year. During SCA, the heart cannot pump efficiently and may beat dangerously fast and/or irregularly. Consequently, blood does not circulate properly to the brain and the other vital organs. According to the American Heart Association (AHA), delivering continuous cardiopulmonary resuscitation (CPR), along with on-time defibrillatory shocks are two main interventions that are likely to restart the arrested heart. A shock advisory algorithm as disclosed herein may advise whether to provide a defibrillatory shock or not provide a defibrillatory shock to the patient based on an evaluation of shockable and non-shockable heart rhythms or ECG signals.

Referring to FIG. 1, an example system 100 for treating a patient 102 with cardiopulmonary issues in accordance with one or more implementations of the present disclosure is shown. Cardiopulmonary issues may relate to the heart 104 and lungs (not shown) of the patient 102. For example, the patient 102 may be suffering from sudden cardiac arrest caused by a function loss of the heart 104. One or more leads 110 may be arranged on the patient 102. For example, the leads 110 may be arranged on the patient 102 (e.g., on the skin surface of the patient 102) to determine an ECG data or electrocardiogram (EKG) data associated with the patient 102 or the heart 104 of the patient 102. The leads 110 may include pads, adhesive, or otherwise, for securing an electrical connection between the patient 102 and the apparatus 120. The leads 110 may comprise a set of leads for measuring the ECG signal or data and a set of leads for providing a defibrillatory shock to the patient 102. The leads 110 may include taps 140 for conveying the ECG signal or data to one or more controllers (e.g., controller 138) of the apparatus 120.

The system 100 may include the apparatus 120 (e.g., an automatic or manual defibrillating device) with circuitry 130. The circuitry 130 may include one or more energy repositories 132, 136, a switch 134, the controller 138, and other components and wiring. The energy repository 132 may be a capacitor or component configured to charge or discharge faster than the energy repository 136. The energy repository 132 may be configured to receive energy from the energy repository 136, which may be a battery or long-term energy storage component. For example, the energy repository 136 may charge or discharge slower than the energy repository 132. The switch 134 may be operable to configure the circuitry 130 to charge the energy repository 132. The switch 134 may be operable to configure the circuitry 130 to discharge the energy repository 132 into the patient 102 (e.g., towards and/or into the patient's heart 104) through the leads 110. The switch 134 may be electromagnetic, solid-state, or otherwise. The circuitry 130 may further include inductors, resistors, capacitors, solid-state logic (e.g., transistors, diodes), wiring, and other elementary components. The switch 134 may be controlled or otherwise operated by the controller 138 through a connection 142. For example, connection 142 may control the switch 134 through a solenoid or solid-state switching mechanism (e.g., MOSFET).

Figure 2:
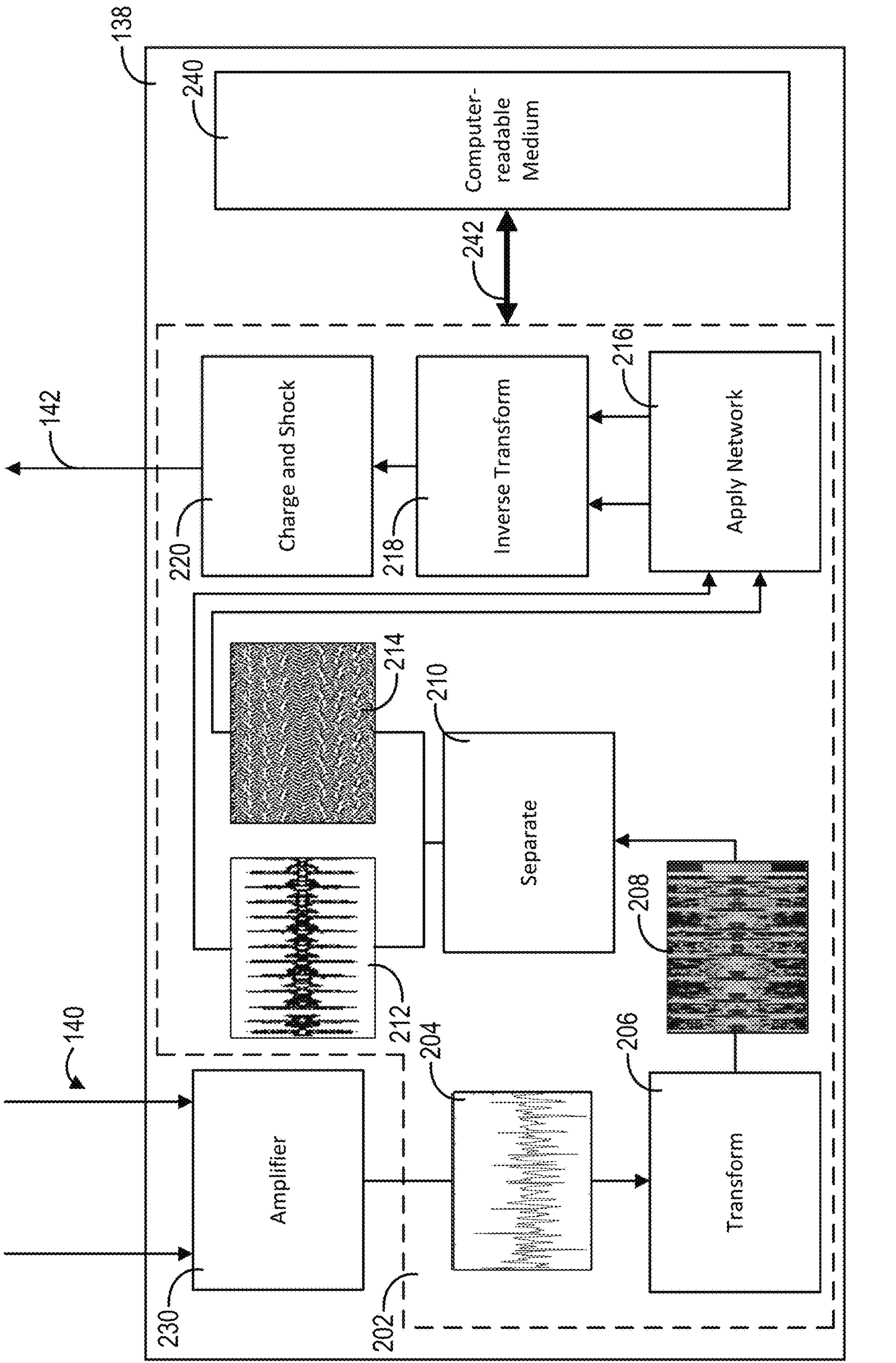
FIG. 2 illustrates an example controller associated with treating a patient in accordance with one or more implementations of the present disclosure.

Referring to FIG. 2, the example controller 138 associated with treating a patient 102 in accordance with one or more implementations of the present disclosure is shown. The controller 138 may include an amplifier 230, a processor 202, and a non-transitory computer-readable medium 240. While the example controller 138 is shown with a single processor, the controller may include one or more processors and may employ, with two or more processors, functions such as parallel computing. Processor 202 may also include one or more amplifiers, including amplifier 230. The computer-readable medium 240 may include instructions 206, 210, 216, 218, 220 disposed thereon and transmitted over a communication bus 242 that when executed by the processor 202 reduce artifacts (e.g., motion artifacts from providing CPR to the patient) of an ECG signal 204, analyze the ECG signal 204 for shockability of the patient 102, or perform other operations associated with the ECG signal 204, circuitry 130 (of FIG. 1), or otherwise.

The processor 202 may receive one or more inputs from the amplifier 230. The amplifier 230 may amplify the signal received from the leads 110 according to the taps 140. As shown, the amplifier 230 may scale, amplify, or otherwise alter the input signal into the ECG signal 204. The processor 202 may convert the ECG signal 204 into data (e.g., ECG data). The data may comprise one or more dimensions based on voltages, currents, or combinations thereof of the ECG signal 204. For example, the data may be an image of the ECG signal 204. The data may be defined as pixels or voxels. A processor or a combination of processors (e.g., processor 202) may be used to conduct processing on the data and define a machine-learning model or process a machine-learning model stored within memory. The machine-learning model may be embedded in a network (e.g., network 300 of FIG. 3) and integrated into processor 202 with a combination of logic, circuitry, and processing.

The processor (e.g., processor 202) may be a combination of various processing types for general processing and machine learning. For example, the processor may include application specific integrated circuits (ASIC), field-programmable gate arrays (FPGA), graphics processing units, central processing units, or combinations thereof. The processing of data may be distributed across various chassis and/or infrastructure. For example, portions of the processing may be conducted in a cloud-computing environment over multiple instances, containers, repositories, or combinations thereof. The machine-learning models and data may be stored over multiple instances, containers, repositories or combinations thereof (e.g., computer-readable medium 240).

As described, instructions may configure the FPGA to transform, inverse transform, separate components, apply a model or network, charge a repository, provide a defibrillatory shock to the patient, or a combination thereof. The instructions may be applied to an ASIC to transform, inverse transform, separate components, apply a model or network, charge a repository, provide a defribrillatory shock to the patient, or a combination thereof. For example, transform 206 may be implemented in an ASIC, and the network 216 may be implemented on an FPGA, all of which (the ASIC and the FPGA) may be generally referred to as a processor with instructions to perform the operations through circuitry. The instructions may ensure the proper initiations, cadence, and completion of tasks associated with the ASICs, FPGAs, other circuitry, processors, or combinations thereof are conducted and completed. For example, instructions may control inputs for ASICs or FPGAs, machine code, assembly code, or higher-level programming languages.

The computer-readable medium 240 may include instructions 206 to transform the data. As an example, the data may be in the time domain. The transform 206 may define the ECG signal 204 in the frequency domain or time-frequency domain. For example, the transform 206 may be based on a Fourier transform. The transform 206 may be a Short-time Fourier Transform (STFT). The transform 206 may output data of an image 208 based on the ECG signal 204 after transformation. The data of the image 208 may show the ECG signal 204 in the time-frequency domain, and the data of the image 208 may be defined as pixels or voxels. Further, the data of the image 208 may be one or more dimension. As discussed herein, image data or data defining an image may be composed of one or more color spectrums (e.g., black and white, grayscale, color), bit depth, and one or more dimensions, and the data may further include metadata.

The computer-readable medium 240 may include instructions 210 to separate the data. The data may be separated into components based on the transform 206. For example, one of the components 212 may be related to the magnitude, absolute value, strength, or otherwise of the time-frequency components within the data of the image 208. The components 212 may be indicated by coloration. For example, as shown on the right-hand side of image 208, component 212 may be indicated by color on a scale where blue is indicative of a relatively low magnitude and red is indicative of a relatively high magnitude. For example, the image 208 may be indicative of frequency over time, where the pulses are shown as higher in frequency and time between pulses is shown in lower frequency. The component 212 may be indicated in greyscale or other implementations as well. For example, the component 212 may be shaded to indicate the magnitude. Another of the components 214 may be related to the phase, angle, or otherwise of the time-frequency within the data of the image 208. The component 214 may be represented in color or grayscale similar or different from the component 212. Other visual representations of the components 212, 214 are contemplated. The instructions 206, 210 may be included in a single function or set of instructions for transforming the ECG signal 204 into one or more of the components 212, 214. The STFT may be normalized and obtained for each data by removing a mean value and dividing by a standard deviation.

The computer-readable medium 240 may include instructions 216 to apply the data to the network. For example, the network may receive data based on the ECG signal 204. The data may be data of the ECG signal 204, data associated with the image 208 based on the ECG signal 204, or the component-based data 212, 214 based on the ECG signal 204. The instructions 216 may include a network architecture, weights, parameters, hyperparameters, or other variables associated with a network or training a network. The network may be trained to remove or reduce artifacts imparted by providing CPR to the patient 102. After the instructions 216 are applied, the prevalence of artifacts related to CPR may be reduced. With the reduced artifact data, instructions 218 may be applied to convert the component-based data 212, 214, data associated with the image 208, or otherwise back into an ECG signal or data of an ECG signal for detection of shockability. For example, an inverse Fourier transform or inverse Short-time Fourier Transform may be applied to the data to convert the network output into an ECG signal. The inverse transform 218 may be based on Equation 3 below. The network may be trained to directly accept the ECG signal 204 or data based on the ECG signal 204, overriding the c.

The computer-readable medium 240 may include instructions 220 to determine the shockability of the patient 102 based on a reduced artifact ECG signal. The instructions 220 may include a classifier to determine whether the patient is shockable over a period (e.g., a rhythm analysis period shown in FIG. 7). For example, the classifier may be trained specifically on data that has a reduced prevalence of artifacts as discussed herein. In such a way the patient 102 may be treated without interrupting the provision of CPR to the patient 102 or with a reduced interruption (e.g., an interruption less than eight seconds). For example, the reduced interruption may be a predetermined quantity of time. The predetermined quantity of time may be based on an accuracy or confidence factor of the ECG signal or based on a quantification of the reduction of artifacts. The instructions 220 may include operation of a digital or analog output of the controller 138 to energize the switch control wire of connection 142. For example, connection 142 may be energized to charge the energy repository 132 for a duration of time based on the ECG signal 204. The connection 142 may be energized to discharge the energy repository 132. The energy repository 132 may be discharged for a duration based on the ECG signal 204. The energy repository 132 may be charged or discharged based on the removed artifacts from the ECG signal 204.

Figure 3:
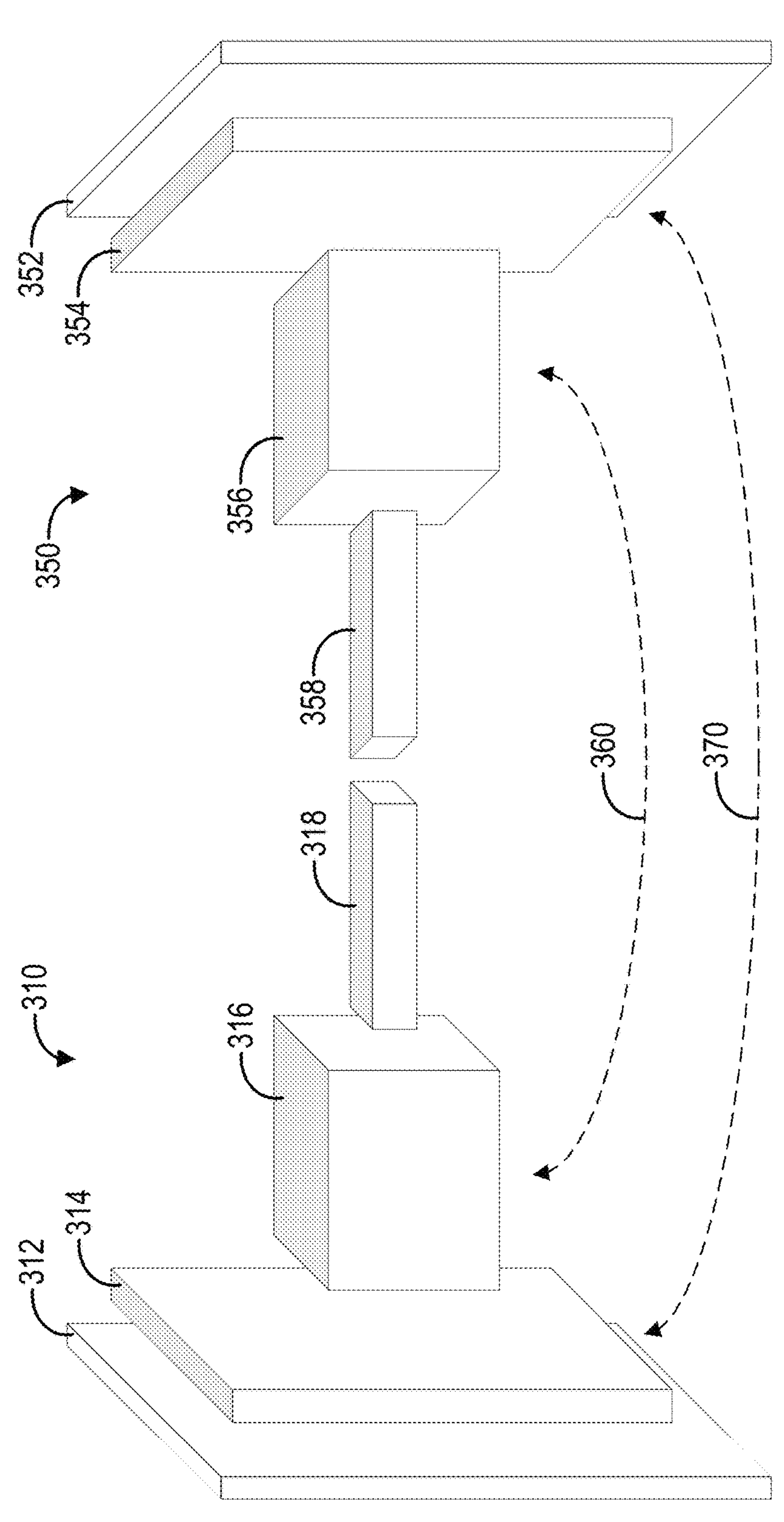
FIG. 3 illustrates an example network in accordance with one or more implementations of the present disclosure.

Referring to FIG. 3, an example network in accordance with one or more implementations of the present disclosure is shown. The network 300 may be defined by an architecture that may include nodes, weights, connections, and other components. The network 300 may be configured with an encoder network 310 or encoder portion and a decoder network 350 or decoder portion. The network 300 may be configured to encode data received at an input layer 312 of the encoder network 300 through layers 314, 316 to an output layer 318 of the encoder network 300. Any quantity of layers may be used.

For example, the input layer 312 may be a 2×128×128 layer (e.g., two channels that received data or images that are 128×128 pixels). The encoder portion may include seven convolutional layers with a convolutional filter size of 3×3 and stride of 2×2. Each convolutional layer may be followed by batch normalization, pooling, activation layers (e.g., ReLu), or combinations thereof. Features may be extracted from the channels through layers 314, 316, 318. More or less than three layers may be used (e.g., seven layers). For example, layers may halve in the x-y dimension (e.g., 128×128 to 64×64) while doubling or increasing in the third dimension (e.g., two channels to eight channels). The output layer 318 may be 512×1×1 providing an input to input layer 358 of the decoder network 350. Features may be upscaled through layers 358, 356, 354, 352 to output layer 352 of decoder network 350 providing a two-channel output having dimensions of 128×128 (e.g., 2× 128× 128). The decoder network 350 may mirror the encoder network 310 having the same quantity and size of layers 352, 354, 356, 358 in reverse order. The network 300 may be trained to receive an ECG signal (e.g., ECG signal 204) and output an ECG signal with reduced artifacts (e.g., motion artifacts from providing CPR to the patient).

The network 300 may further include skip connections (e.g., skip connections 360, 370) between one or more layers of the encoder network 310 and the decoder network 350. Details of the signal characteristics of the ECG signal 204 may have been lost over the encoder network 310 because of the layers 312, 314, 316, 318 and the skip connections 360, 370 may be applied between corresponding convolutional and transposed convolutional layers to directly pass the signal and feature information from the encoder network 310 to the decoder network 350. The skip connections 360, 370 may also reduce vanishing gradients when the network 300 is deep with numerous layers.

Figure 4:
FIG. 4 illustrates an example method for treating a patient with cardiopulmonary issues in accordance with one or more implementations of the present disclosure.
Figure 4:
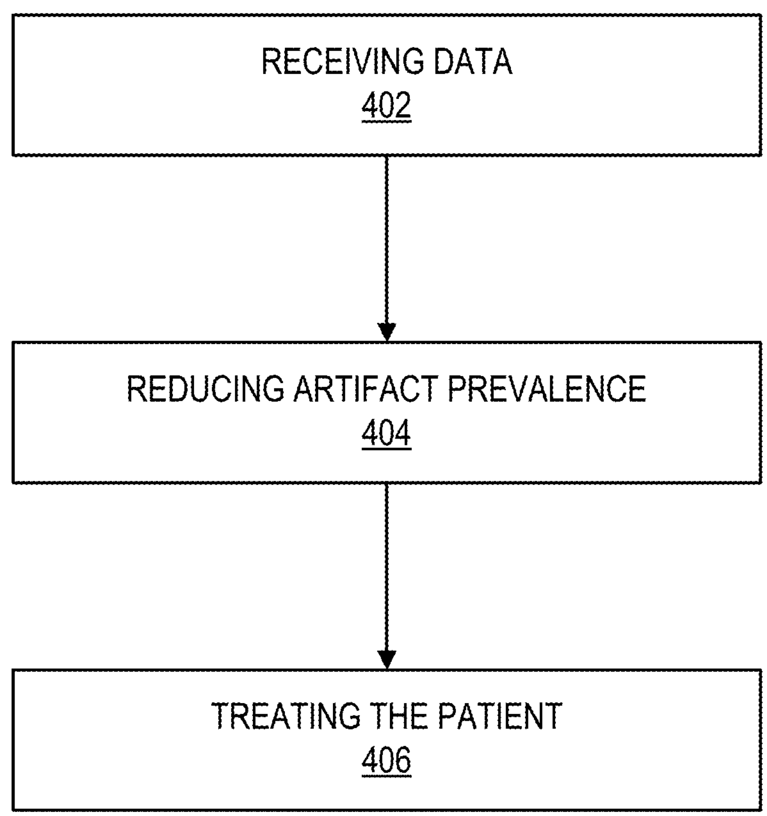

In FIG. 4, an example method 400 for treating a patient with cardiopulmonary issues in accordance with one or more implementations of the present disclosure is shown. Data may be received in step 402. The data may be received based on an ECG signal (e.g., ECG signal 204) according to leads 110. For example, the leads 110 may be attached to the patient 102. The data may be a two-dimensional image of a Fourier transform of the ECG signal (e.g., the image 208). The data may be images of components of the Fourier transform (e.g., the components 212, 214). The data may be encoded based on the encoder network 310 or network 300.

The input ECG signal may include artifacts, and the artifacts may be imparted onto the input ECG signal by providing CPR or other life-saving actions performed by medical responders. For example, the artifacts may increase or decrease the ECG signal (e.g., voltage of the signal) with every compression or decompression provided to the patient 102 while providing CPR. For example, the artifacts may be motion artifacts. For example, the artifacts may be based on an environmental condition that biases the ECG signal (e.g., weather, temperature, wind, humidity). The network 300 may decode the data in a way that reduces the prevalence of artifacts. For example, the data may be decoded by the decoder network 350.

In step 404, artifact prevalence may be reduced. The artifact prevalence may be reduced based on the original ECG signal and an outputted ECG signal. For example, the original ECG signal (e.g., ECG signal 204, the unamplified ECG signal from leads 140) may be compared with an output ECG signal (e.g., a signal defined by the inverse transform 218 and network 300) as an indication of artifact reduction. Features within the original ECG signal may be indicative of artifacts, a reduction in those features may be indicative that the prevalence of the artifacts was reduced. For example, features within the ECG signal may be indicative of artifact reduction (e.g., less prevalence of those features when subsequently encoded by encoder 310). For example, the features may have an activation that is lower based on the network 300 or a percentage of those features that are not expressed in one or more layers of the network (e.g., encoder 310). The encoder output may be indicative of the quantity of features in the ECG signal related to artifacts. Features may be represented in the layers or weights of the encoder 310 or one or more of the layers or weights of the encoder 310 may be indicative of the features. The method 400 may include using a Fourier transform to determine the data. The method 400 may include using components of the Fourier transform to determine the data. In addition, the data may be encoded based on a network and decoded based on the network to remove the artifacts from the original ECG signal (e.g., ECG signal 204 or other data representative of an ECG signal or portion thereof).

In step 406, the patient 102 may be treated. For example, the patient 102 may be shocked by circuitry 130. The method 400 may include determining whether the patient 102 is shockable or whether an ECG rhythm of the patient 102. The ECG rhythm of the path may indicate that it is the correct time to shock the patient.

For example, the method 400 may include determining that the patient 102 or the ECG rhythm of the patient 102 is shockable and charging the energy repository 132 based on that determination. Whether a patient is shockable may be based on the ECG signal, safety associated with the shock, a likelihood of success of the shock, and other factors. The charging of the energy repository 132 may be based on a likelihood of success of the shocking treatment to treat defibrillation of the heart 104 of the patient 102. For example, an algorithm may be used to determine whether the patient is shockable with a level of certainty or likelihood. If that likelihood satisfies a threshold (e.g., 70%), the energy repository 132 may be charged, discharged, or a combination thereof. The ECG signal 204 may indicate fibrillation while CPR is being performed on the patient 102 or within eight seconds of CPR being performed on the patient 102. CPR may be stopped to allow the patient 102 to receive a defibrillatory shock.

Figure 5:
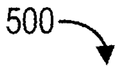
FIG. 5 illustrates an example method for training one or more networks in accordance with one or more implementations of the present disclosure.
Figure 5:
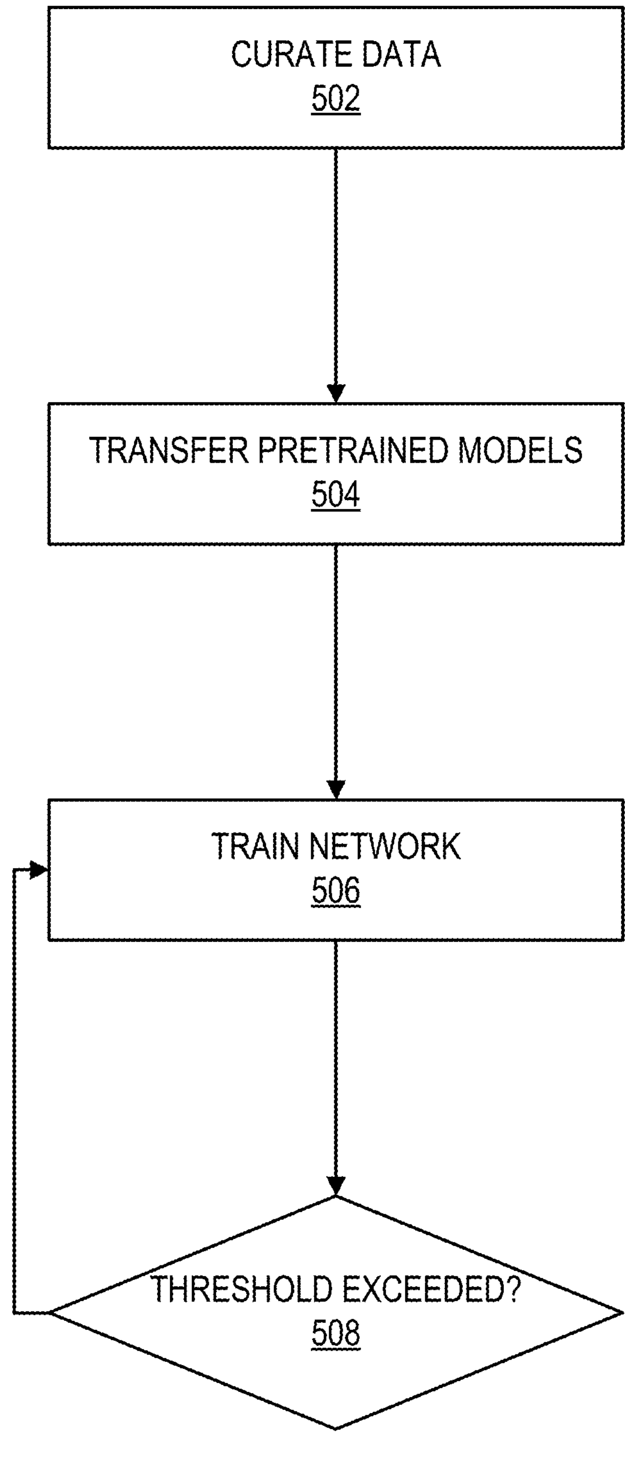

In FIG. 5, an example method 500 for training one or more networks (e.g., encoder network 310, decoder network 350, network 300) in accordance with one or more implementations of the present disclosure is shown. The method may be performed on one or more computing systems described herein (e.g., in the cloud). Further, the trained network 500, or portion thereof, may be trained and ported to an ASIC or FPGA.

The method 500 includes curation of training data and testing data in step 502. For example, data for training the network 300 may include examples of the ECG signals during an interruption (e.g., clean signals without artifacts) and examples of ECG signals with artifacts. For example, the examples may be 14-second ECG segments. The examples may be images. For example, the examples may be transformed for training as described herein. The examples may be separated into training data and testing data for steps 506, 508.

The training dataset may include paired ECG data (e.g., clean-clean, artifact-clean). For example, ECG recordings may have a sampling frequency of 250 Hz with a 12-bit resolution over a 10 millivolt (mV) range. In order to have more different types of non-shockable data, portions of additional recordings with only non-shockable rhythms may be used. For example, non-shockable data or non-shockable rhythms may include data that is indicative that the shock will be unsuccessful in defibrillation based on a likelihood. Recordings may be curated from multiple databases to improve the diversity of non-shockable rhythms by adding different patterns of atrial fibrillation (AF) rhythms. The images may be annotated by visual confirmation by trained ECG experts to label both shockable and non-shockable samples to create, for example, 14-second artifact-free ECG samples. The artifact-free ECG samples may be combined with CPR artifacts to generate the corresponding CPR-contaminated data. In addition, asystole data from different patients while CPR is being performed on those patients by different rescuers may be collected using existing defibrillation devices. ECG samples may be obtained with CPR artifacts. The defibrillation sampling frequency may be, for example, 125 Hz. All data may be converted to have a uniform sampling rate (e.g., a sampling rate of 125 Hz). CPR-contaminated ECG samples may be generated by combining every clean ECG sample with different CPR artifacts (e.g., 37 different CPR artifact types). Since there may be a disproportionally higher number of non-shockable than shockable data, oversampling the minority class (randomly replicating the samples) and undersampling the majority class (randomly removing samples) to correct the imbalance may be performed such that the balanced training set includes the same number of samples for each class (shockable and non-shockable).

In step 504, the network may be pre-trained with weights from non-ECG data. For example, the network may be pre-trained with images unrelated to ECGs. In step 506, the network 300, or individual networks (e.g., encoder network 310 or decoder network 350) may be trained according to the training data described herein until an error threshold is exceeded. Artifact-reduced ECG estimation may be considered as non-linear mapping from input data to the desired output. This mapping can be better reflected by following equations:

$$y = f^e(w^e x + b^e) \tag{1}$$

$$\hat{x} = f^d(w^d y + b^d) \tag{2}$$

Equation (1) represents the encoder section of network 300, which learns to extract high level features from time-frequency representations of CPR-contaminated input data. In Equation (1), the terms $w^e$ and $b^e$ are the weight matrix and a bias vector between input data x and a hidden representation y of the encoder network 310, respectively. $f^e$ is a nonlinear mapping function for the encoder network 310. The decoder network 350 is responsible for the reconstruction process and learns to capture time-frequency representations of the desired artifact-reduced ECG, which is expressed in one or more ways by Equation (2). In Equation (2) $w^d$, $b^d$ are the weight and a bias between the hidden representation y and the reconstructed output $\hat{x}$. Similarly, $f^d$ is a nonlinear mapping function for decoder network 350. The parameters of Equations 1 and 2 are optimized during the training phase by minimizing the error between the desired output and the input. An optimizer may be used to perform the training. For example, an optimizer with the parameters of $\beta_1$=0.9, $\beta_1$=0.999 and a mini batch size of 128 may be used for optimizing the network. The optimizer may be an ADAM optimizer. The initial learning rate may be 0.001, and it may be decreased, for example, every four epochs by a drop factor of 0.1.

In step 508, the network 300 may be evaluated. The error may be different for shockable and non-shockable rhythms. The CPR-contaminated ECGs from the test dataset may be used to examine the efficacy of the trained network using signal-to-noise-ratios (SNR), correlation coefficients, a shock advisory algorithm (SAA), or combinations thereof. The test dataset may include data similar to that of the training dataset, except the network 300 may be trained with the training dataset and tested with the testing dataset. To reconstruct the signal, it may be required to transfer the angular form of the spectrograms back to the rectangular form using the absolute value and angle of Equation (3):

$$\widehat{STFT} = \text{abs}_{\widehat{STFT}}.\text{Cos}(\text{angle}_{\widehat{STFT}}) + j \times \text{abs}_{\widehat{STFT}}.\text{Sin}(\text{angle}_{\widehat{STFT}}) \quad (3)$$

The normalized STFT may be then mapped back to the original signal (e.g., ECG signal 204 using pre-saved mean and standard deviation values. Finally, an artifact-reduced ECG may be constructed by applying the inverse STFT transform (e.g., inverse transform 218) to the reduced artifact data from network 300. These results may be provided of a continuous and accurate AED rhythm analysis without stoppage of CPR using only ECG data. Once the error threshold is exceeded, the network 300 may be considered trained. Equations 1, 2, or 3 may be used in various aspects throughout this disclosure.

Figure 6:
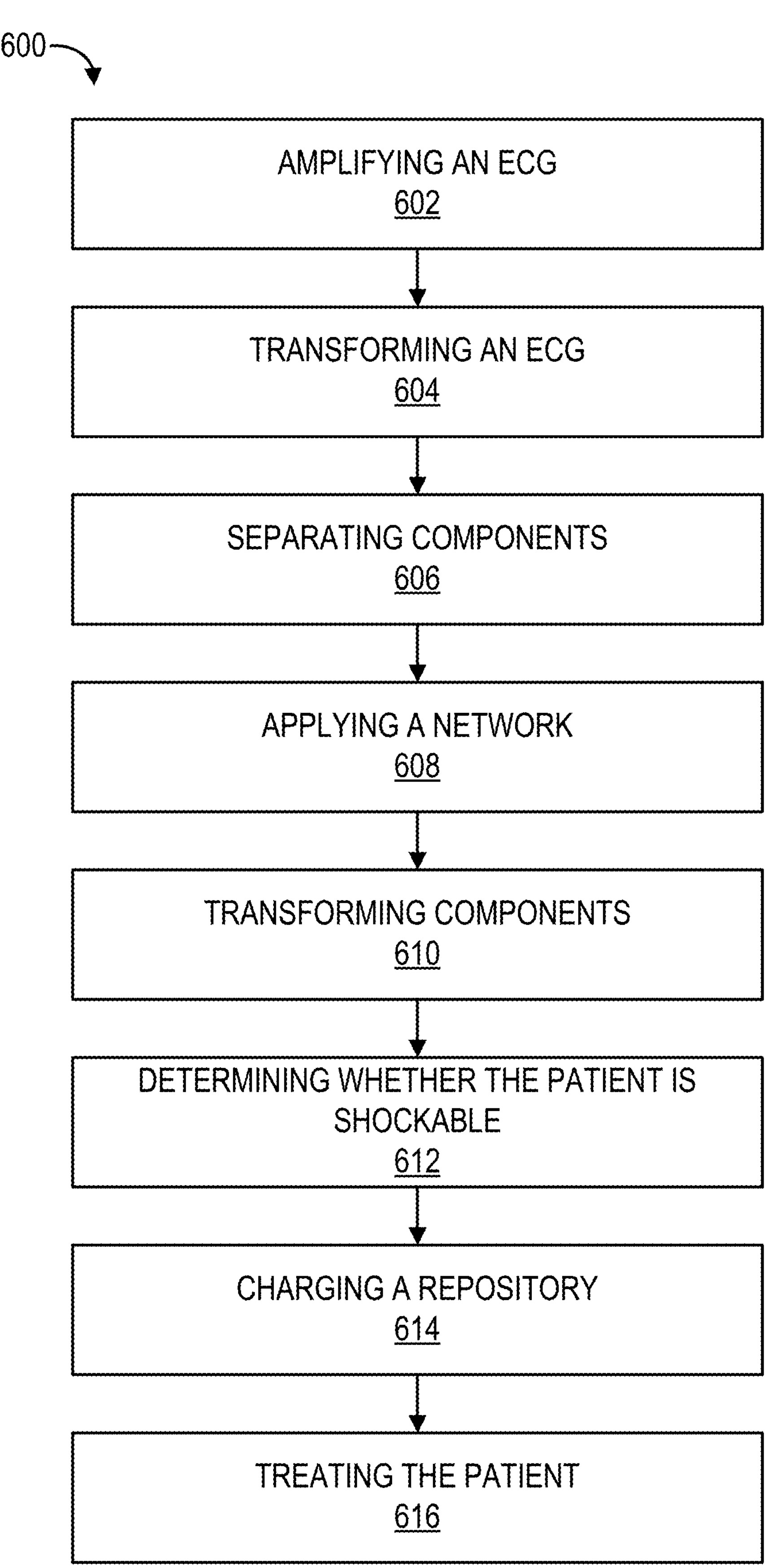
FIG. 6 illustrates an example method for treating a patient in accordance with one or more implementations of the present disclosure.

Referring to FIG. 6, an example method 600 associated with treating a patient 102 in accordance with one or more implementations of the present disclosure is shown. The method 600 may be implemented on one or more controllers as described with regard to FIG. 2 (e.g., controller 138), and the controller may include ASICs, FPGAs, other processing components, or combinations thereof. In step 602, an unamplified ECG signal from taps 140 may be amplified into ECG signal 204. Amplification may scale, amplify, or otherwise alter the input signal (e.g., an unamplified ECG signal) into ECG signal 204. Amplification may include converting the ECG signal 204 into data. The data may be one or more dimensions based on voltages, currents, or combinations thereof of the ECG signal 204. For example, the data may be an image of the ECG signal 204. The data may be defined as pixels or voxels.

In step 604, the data or signal (e.g., ECG signal 204) may be transformed, for example, by the transform 206. For example, the signal (e.g., ECG signal 204) or data may be in the time domain and transformed into the frequency domain. A Fourier transform may be used. The transform may be a Short-time Fourier Transform (STFT). The transform (e.g., transform 206) may output data of an image 208 based on the ECG signal 204 after transformation. The data of the image 208 may show the ECG signal 204 in the time-frequency domain, and the data of the image 208 may be defined as pixels or voxels. Further, the data of the image 208 may be one or more dimension. As discussed herein, image data or data defining an image may be composed of one or more color spectrums (e.g., black and white, grayscale, color), bit depth, and one or more dimensions, and the image data may further include metadata.

In step 606, the data (e.g., image data) may be separated into components (e.g., components 212, 214). The data may be separated into components based on the transform (e.g., transform 206). For example, one of the components 212 may be related to the magnitude, absolute value, strength, or otherwise of the time-frequency components within the data of the image 208. The component 212 may be indicated by coloration. For example, as shown on the right-hand side of image 208, component 212 may be indicated by color on a scale where blue is indicative of a relatively low magnitude and red is indicative of a relatively high magnitude. For example, the image 208 may be indicative of frequency over time where the pulses are shown as higher in frequency and time between pulses is shown in lower frequency. The component 212 may be indicated in greyscale or other implementations as well. For example, the component 212 may be shaded to indicate the magnitude of the component. Another of the components 214 may be related to the phase, angle, or otherwise of the time-frequency within the data of the image 208. The component 214 may be represented in color or grayscale similar or different from the component 212. Any visual representation of components 212, 214 is contemplated. The STFT may be normalized and obtained for each data by removing the mean value of the data and dividing by the standard deviation of the data.

In step 608, a network may be applied to remove artifacts from providing CPR to the patient 102. For example, a trained network (e.g., network 300) as described herein may be used to remove artifacts. For example, the network may receive data based on the ECG signal 204. The data may be data of the ECG signal 204, data associated with the image 208 based on the ECG signal 204, or component-based data 212, 214 based on the ECG signal 204. Applying the network may be based on one or more network architecture, weights, parameters, hyperparameters, or other variables associated with a network or training a network. The network may be trained to remove or reduce artifacts imparted on the original, unamplified ECG signal by providing CPR to the patient 102. After step 608, the prevalence of artifacts related to providing CPR to the patient may be reduced.

In step 610, the components or component data 212, 214 may be transformed in an ECG signal. For example, with the reduced artifact data, a transform inverse to that of transform 206 may be applied to convert the component-based data 212, 214, data associated with the image 208, or otherwise back into an ECG signal with reduced artifact prevalence or data of an ECG signal for detection of shockability. For example, an inverse Fourier transform or inverse Short-time Fourier Transform may be applied to the data to convert the network (e.g., network 300) output into an ECG signal with reduced artifact prevalence. The inverse transform may be based on Equation 3.

In step 612, the patient may be determined to be shockable or unshockable based on signals or data from one or more of the previous steps. For example, the shockability may be determined based on the reduced-artifact ECG signal. Shockability may be determined based on a classifier. For example, the classifier may be trained specifically on data that has a reduced prevalence of artifacts as discussed herein. In such a way the patient 102 may be treated without interruption of CPR or with a reduced interruption (e.g., an interruption less than eight seconds). That is, the treatment may be applied before the motion artifacts from CPR would naturally subside from an interruption to CPR applied to the patient. For example, the reduced interruption may be a predetermined quantity of time. The predetermined quantity of time may be based on an accuracy or confidence factor of the reduced-artifact ECG signal or based on a quantification of the reduction of artifacts.

In step 614, the energy repository 132 of the apparatus 120 (e.g., an automatic or manual defibrillating device) may be charged. For example, a digital or analog output of the controller 138 may be used to energize the switch control wire of connection 142, resulting in the energy repository 132 being charged. Charging the energy repository 132 may be for a duration based on the ECG signal 204.

In step 616, the patient 102 may be treated. Treatment of the patient 102 may include medications or physical intervention (e.g., defibrillatory shocking). For example, connection 142 may be energized to discharge the energy repository 132. The energy repository 132 may be discharged for a duration based on the ECG signal 204. The energy repository 132 may be charged or discharged based on the removed artifacts from the ECG signal 204.

Figure 7:
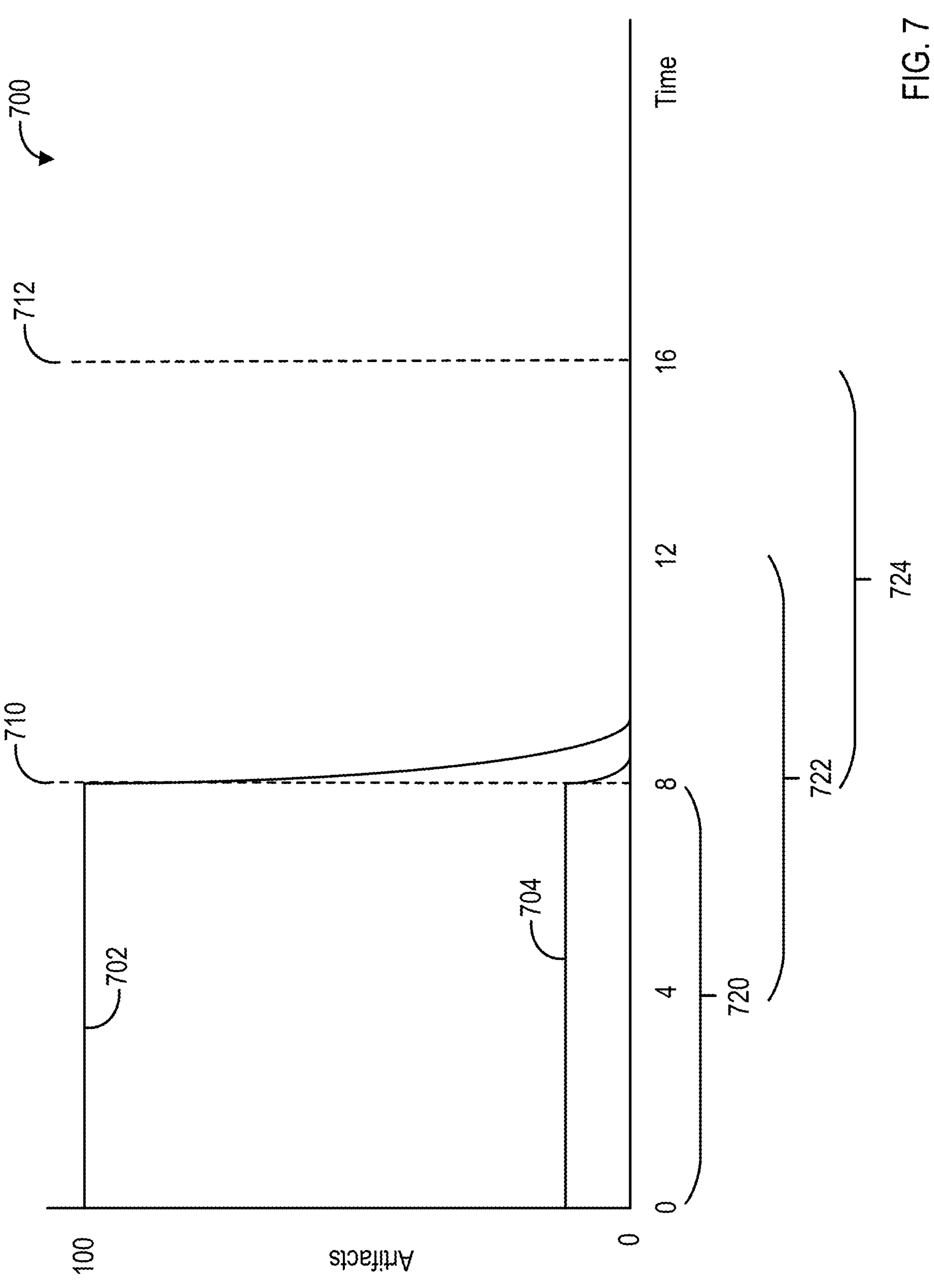
FIG. 7 illustrates an example treatment sequence for treating a patient in accordance with one or more implementations of the present disclosure.

In FIG. 7, an example treatment sequence 700 for treating a patient in accordance with one or more implementations of the present disclosure is shown. For example, the quantified artifacts 702 may be imparted by cardiopulmonary resuscitation in an ECG signal (e.g., ECG signal 204). For comparison, a prevalence of artifacts in an ECG signal (e.g., ECG signal 204) may be reduced (to quantified artifacts 704) as described herein and converted to a clean or cleaner ECG signal by instructions (e.g., instructions 206, 210, 216, 218). The instructions (e.g., instructions 206, 210, 216, 218) may reduce or remove the prevalence of artifacts (e.g., quantified artifacts 704).

As cardiopulmonary resuscitation is interrupted at time 710, the quantified artifacts 702, 704 from cardiopulmonary resuscitation may subside. To assess whether the patient can be shocked to improve health or situation, a rhythm analysis period 720 may be used to assess the clean, or cleaner, ECG signal. For example, the rhythm analysis period may require a duration (e.g., eight or fourteen seconds) of the clean, or cleaner, ECG signal with reduced artifacts (e.g., quantified artifacts 704) to accurately determine whether the patient is shockable. That is, rhythm analysis may be required to wait until the artifacts (e.g., quantified artifacts 702) imparted by cardiopulmonary resuscitation subside after the interruption at time 710.

The rhythm analysis period (rhythm analysis period 720, 722, 724) may occur before, during, or after the interruption of cardiopulmonary resuscitation at time 710. As such, treatment on the patient may commence (e.g., charge an energy repository, shock the patient 102, or combination thereof) within less than eight seconds (e.g., time 712) from the interruption to cardiopulmonary resuscitation at time 710.

Further discussion is now presented that provides increased accuracy in determining a shock/no-shock decision. To provide context, current American Heart Association (AHA) guidelines call for a two-minute period of CPR prior to every pause for rhythm analysis for AEDs. These conventional AED algorithms require interruptions of CPR for ECG rhythm analysis, shock or no-shock decision, and defibrillator charging and shock delivery, as shown in FIG. 8. FIG. 9 illustrates examples of embodiments for elimination of the pause in CPR during analysis for shockable rhythms (FIG. 9A) and non-shockable rhythms (FIG. 9B). Additionally, in cases where the initial decision is deemed unreliable, a prudent approach is to wait for another CPR-contaminated ECG segment (i.e., still no pause taken in CPR) and apply the conventional algorithm again, or in the worst scenario stopping the CPR and waiting for a clean segment (i.e., without artifacts from CPR due to cessation thereof) to ensure a trustworthy and dependable decision (FIG. 9C).

To overcome the limitations of conventional AEDs and associated algorithms, a Convolutional Neural Network-based Encoder-Decoder (CNNED) structure specifically designed to efficiently remove the CPR artifact may be used. The CNNED structure (for example, a non-transitory set of machine executable instructions) provides for further improving the accuracy of shock advisory algorithms in AEDs during ongoing CPR. The CNNED structure may be implemented by the controller 138 illustrated in FIGS. 1 and 2. This approach involves the use of imbalanced shockable and non-shockable training data to better remove CPR-contaminated ECG signals. First, the CPR-contaminated ECG segment is denoised using balanced training data, rhythms are identified, and they are classified as either shockable or non-shockable in a first CNNED block. Then, the reconstructed signal is subjected to another or second denoising CNNED block that is specific to the type of rhythm seen in the ECG segment; hence, the training data are imbalanced in favor of the classification of rhythm present. For example, if shockable rhythms, the training data may include significantly more shockable than non-shockable and vice versa for non-shockable rhythms. The second use of CNNED (i.e., the second CNNED block) makes small adjustments to the dynamics of the signal and tests whether the reconstructed ECG still falls under the same classification as the first use of CNNED (i.e., the first CNNED block). If there is a change in the classification outcome, the reconstructed signal from the first pass is deemed unreliable, and the segment is considered as indeterminate. This approach allows for a more accurate classification of shockable and non-shockable rhythms during CPR, potentially leading to improved patient outcomes. Details are provided below.

Figure 10:
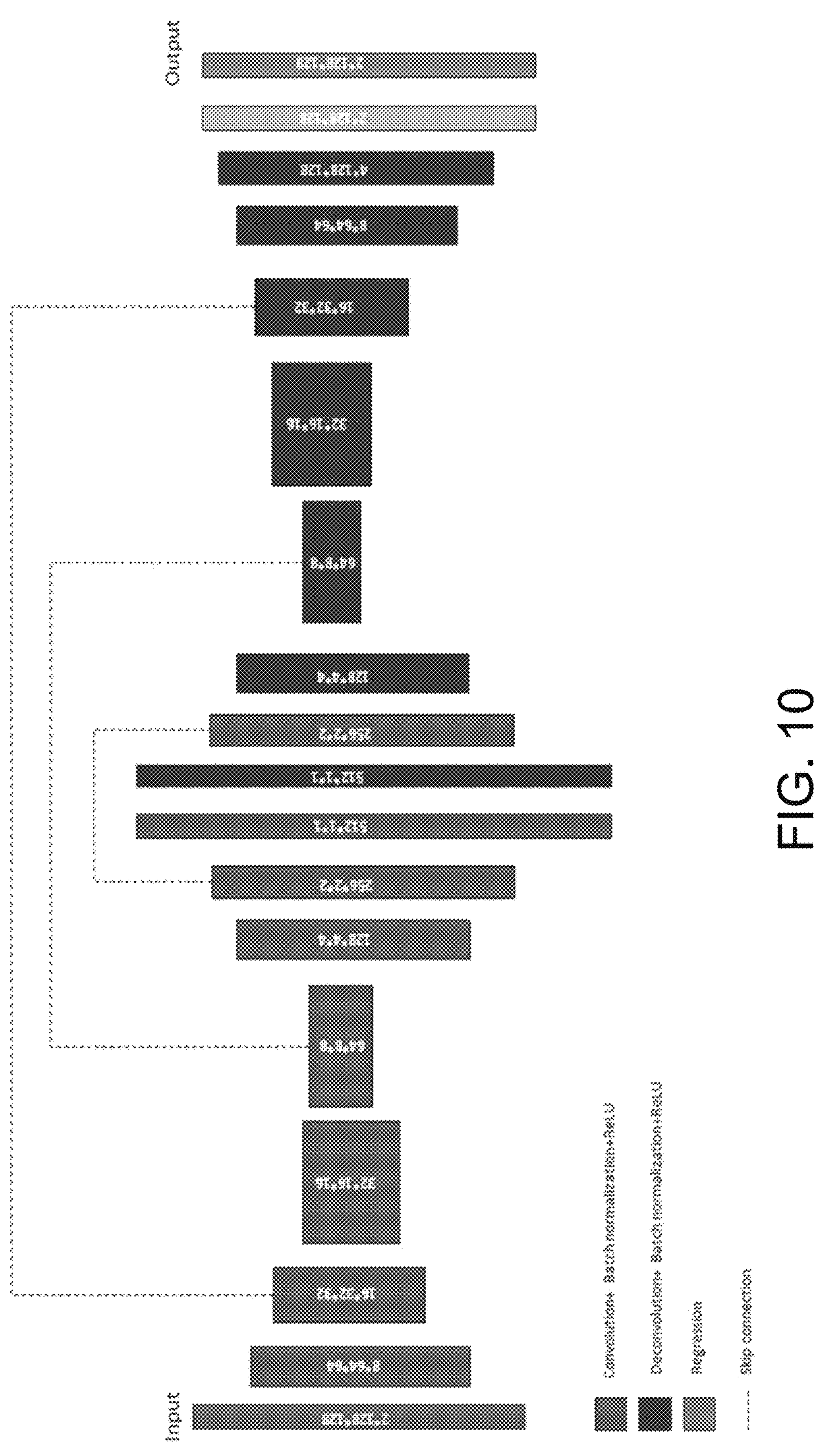
FIG. 10 illustrates a schematic overview of the CNNED structure.

The CNNED structure for the first and second CNNED blocks use time-frequency spectral information as the input. Specifically, the encoder portion of the CNNED uses the magnitude and phase contents derived via time-varying spectral analysis to learn distinct features that are representative of both the ECG signal and CPR artifacts. The decoder portion takes the results from the encoder and reconstructs what is perceived as the motion artifact-removed ECG data. FIG. 10 illustrates the structure of the CNNED. Also, for the hyperparameters, an Adam optimizer function to optimize the cost function is used for hyper-tuning. The initial learning rate was set to 0.001 and then decreased every 4 epochs by a drop factor of 0.1. However, for minibatch size 64 is used instead of 128.

While ECG waveforms and the frequency content of the shockable and non-shockable data groups are different in most cases, their dynamics do overlap in certain arrhythmias (e.g., between supra VT and VT). Moreover, if CPR artifacts are not completely and accurately removed, the residual CPR artifacts may mask the true underlying dynamics. Hence, in these scenarios, a CNNED model trained on an equal number of shockable and non-shockable rhythms may not be able to differentiate the true nature of the arrhythmia. While the approach using equal numbers of shockable and non-shockable rhythms for training does provide good results in most cases, as shown in Table 2, the results can be further improved by using the scheme illustrated in the flowchart of FIG. 11, for the reasons described above.

Figure 11:
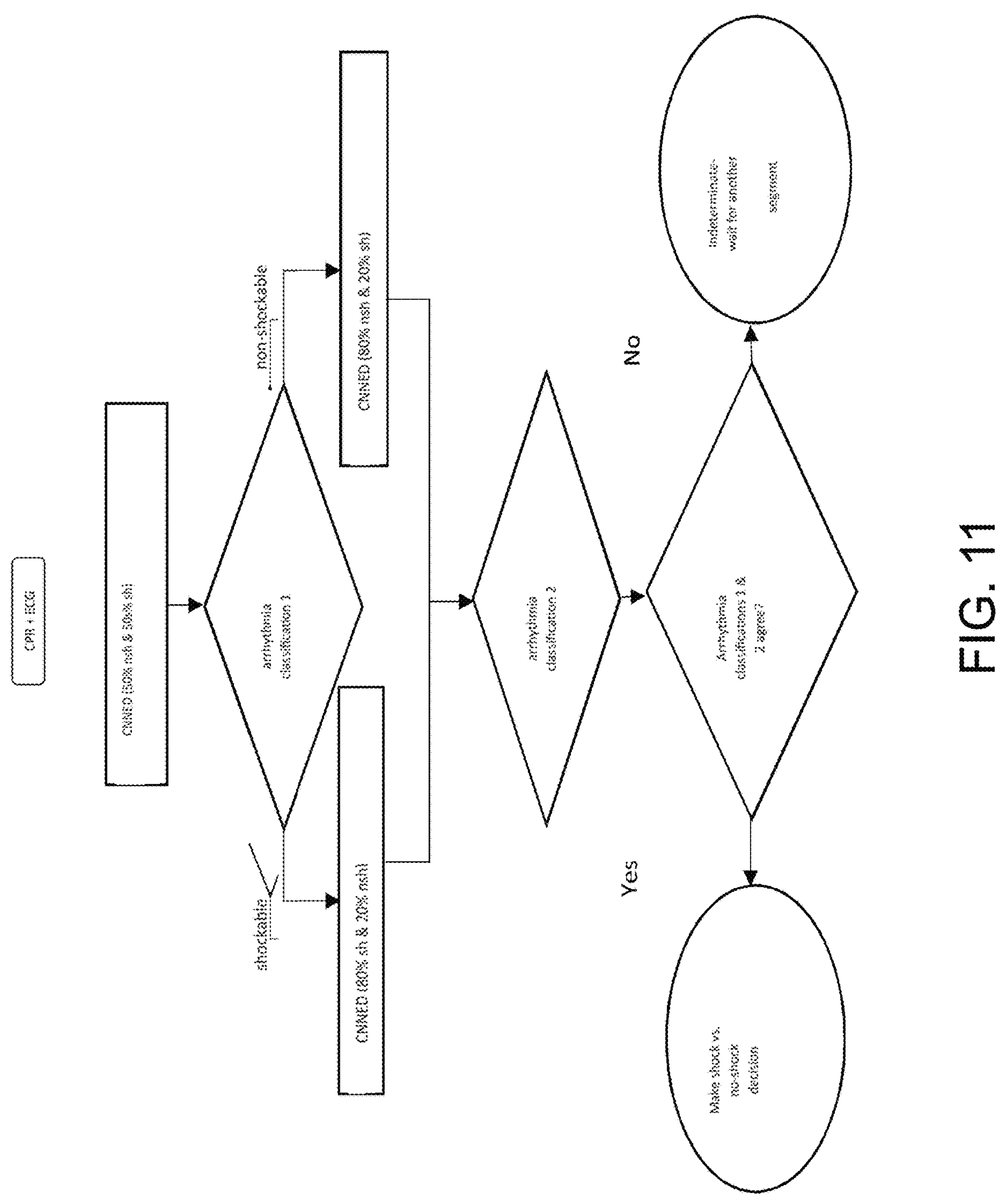
FIG. 11 is a flowchart depicting aspects of using the CNNED structure to discriminate between shockable (sh) and non-shockable (nsh) arrhythmia events.

FIG. 11 is a flowchart illustrating the use of CNNED to discriminate between shockable (sh) and non-shockable (nsh) arrhythmia. The main idea of this new novel approach of having cascades of CNNED is to train for shockable rhythms with more shockable data than non-shockable, and vice versa for non-shockable rhythms. For example, for CNNED specific to shockable, 80% shockable data and 20% non-shockable data were used for training. The reverse percentages were used for training a CNNED model specific to non-shockable rhythms. This distribution of shockable and non-shockable for CNNED specific to shockable and vice versa for non-shockable was found to be optimal, as shown in Table 1, which is described in detail below. Accordingly, two specific CNNED models are employed, trained individually for each class by training predominantly with the congruous data type. Note that the architecture of the class-specific CNNED models is the same as the CNNED trained with an equal number of shockable and non-shockable data. The discussion below further explains the scenarios discussed when the novel approach in FIG. 11 is applied to CPR data.

TABLE 1

Results on CNNEDs with various imbalanced training data schemes.

| CNNED model training data proportion for each rhythm class | Specificity | Sensitivity | Accuracy | Percentage of Inconclusive decisions |
|---|---|---|---|---|
| 70nsh %-30sh %, 30nsh %-70sh | 97.83% | 90.40% | 96.75 | 5.63% |
| 80nsh %-20sh %, 20nsh %-80sh | 98.16 | 92.15% | 97.27 | 3.35% |
| 90nsh %-10sh %, 10nsh %-90sh | 98.05 | 92.17 | 97.17 | 4.58% |

TABLE 2

Comparison of classifier performance on unfiltered ECG

| Rhythm | AHA's performance goal on artifact-free ECG | Results on unfiltered ECG | CNNED + arrhythmia classification | New approach |
|---|---|---|---|---|
| Shockable | | | | |
| Course VF | >90% SE | 67.68% SE | 90.90% SE | 95.41% SE |
| Rapid VT | >75% SE | 62.71% SE | 82.26% SE | 87.66% SE |
| Non-shockable | | | | |
| NSR | >99% SP | 96.21% SP | 99.14% SP | 99.35% SP |
| AF, SB, SVT, RSVT, PVC | >95% SP | 88.5% SP | 96.45% SP | 97.22% SP |

Data in Table 2 developed using 50%-50% CNNED and disclosed approach. SE=sensitivity, SP=specificity, NSR: normal sinus rhythm, AF: atrial fibrillation, SB: sinus bradycardia, SVT: supra-ventricular tachycardia, RSVT: rapid supraventricular tachycardia, PVC: pre-mature ventricular contraction.

In practice, since it is not known a-priori if CPR-contaminated data contain shockable rhythms or not, it is needed to first run CNNED trained with equal data distributions of shockable and non-shockable rhythms. Then arrhythmia classification algorithms are run to determine the classification of shockable vs. non-shockable. The 4th column of Table 2 indicates the performance for this part. If shockable, the CNNED specifically trained for shockable and similarly for non-shockable is deployed. FIG. 10 illustrates the framework for applying the specific CNNED models on shockable and non-shockable ECG data segments. This second use of CNNED (after arrhythmia classification 1) is mainly for further validation of the first CNNED's efficacy in removing CPR artifacts and the resultant shock vs. non-shock classification. When shockable data classified from the first use of CNNED, followed by arrhythmia classification, are subjected to the second CNNED specific to shockable (trained with 80% shockable and 20% non-shockable), most of the data are confirmed to be shockable. The same outcome occurs for non-shockable training data, and similarly for non-shockable, hence, the first classification decision holds for the vast majority of data. However, there are some minor cases for which the decision will be reversed after the second use of CNNED. That is, a shockable rhythm per the first (50%/50%) CNNED will be classified as non-shockable after the second CNNED. Or, a rhythm first determined to be non-shockable by the first (50%/50%) CNNED model will be determined to be shockable by the second use of CNNED, even though that second use was trained on 80% non-shockable data. These decision reversals, albeit in a minority of cases, cast doubt on the signal quality of the output of the first use of CNNED. Hence, the reversal of the initial decision after the second use of CNNED is considered an indeterminate classification. The way to combat these indeterminate cases is to wait for additional data (~7-14 s of new data) and go through the entire process in FIG. 10 again, or in the worst scenario stopping the CPR and waiting for a clean segment.

As discussed above, the CPR-contaminated ECG signal is fed into the CNNED that has been trained using balanced data. The output of this CNNED is then passed to the first classifier to determine if the segment is non-shockable or shockable. If the segment is classified as non-shockable, it is then fed into the CNNED that has been trained on imbalanced data biased towards non-shockable segments. The signal is reconstructed and then passed again to an arrhythmia classifier. Since the reconstruction step is biased towards non-shockable dynamics, it is not expected that any significant change in the decision of the second classifier. If there is a change in the decision of the second classifier, the decision is considered unreliable and it is labeled as indeterminate. In such cases, another segment is required for further analysis.

If the decision of the first classifier is shockable, a similar procedure is followed as before, but with the difference that the signal is fed into the CNNED which is biased towards the dynamics of shockable rhythms.

This novel approach used ECG recordings from various online datasets. All of these datasets had a sampling frequency of 250 Hz and a 12-bit resolution over the 10 mV range. To add more diversity, 20 additional recordings with non-shockable data were used. Furthermore, 21 recordings from an arterial fibrillation data base (AFDB) dataset, including AF segments, were added to the dataset. To train the novel model, ECGs both with and without CPR artifacts were needed, so the artifact-free ECG samples were combined with CPR artifacts to generate the corresponding CPR-contaminated data. To do this, asystole data was collected from 52 different patients during CPR performed by various rescuers using AED devices. The AEDs had a sampling frequency of 125 Hz, so all above ECG samples from the various databases were resampled to 125 Hz. Subsequently, CPR-contaminated ECG samples were generated by combining each clean ECG sample with 37 different CPR artifact cases for the test set. The 52 CPR samples were divided into 37 for the training set and 15 samples for the validation set.

To train the first CNNED to remove the significant CPR artifacts, the same training approach was used as discussed above with an equal distribution of 50% non-shockable and 50% shockable data in the training set.

To train the imbalanced CNNEDs, the denoised output of the first CNNED was used, which had been trained using a 50/50 ratio of non-shockable to shockable data. For the CNNED which is designed and trained for non-shockable rhythms, it was trained on imbalanced data, where non-shockable segments were four times more prevalent than shockable segments. Conversely, for the CNNED which is designed and trained for shockable rhythms, it was trained on imbalanced data where shockable segments were four times more prevalent than non-shockable segments.

To evaluate the performance of the trained CNNED network, testing was conducted using ECG recordings collected from AEDs in combination with various CPR artifacts. The clean ECG dataset included non-shockable rhythms from 396 subjects, including NSR, VT, supra VT, rapid supra VT, sinus bradycardia, AF, AFL, heart block, and PVCs. Additionally, shockable rhythms from 72 subjects were included, consisting of rapid VT and VF. All recordings were sampled at a frequency of 125 Hz.

To create the test dataset, the same procedure was used as discussed above. Clean ECG segments were combined with the 52 different CPR artifact cases. This process generated a separate test set consisting of 20,384 CPR-contaminated non-shockable ECG samples and 3744 CPR-contaminated shockable ECG samples.

Figure 12:
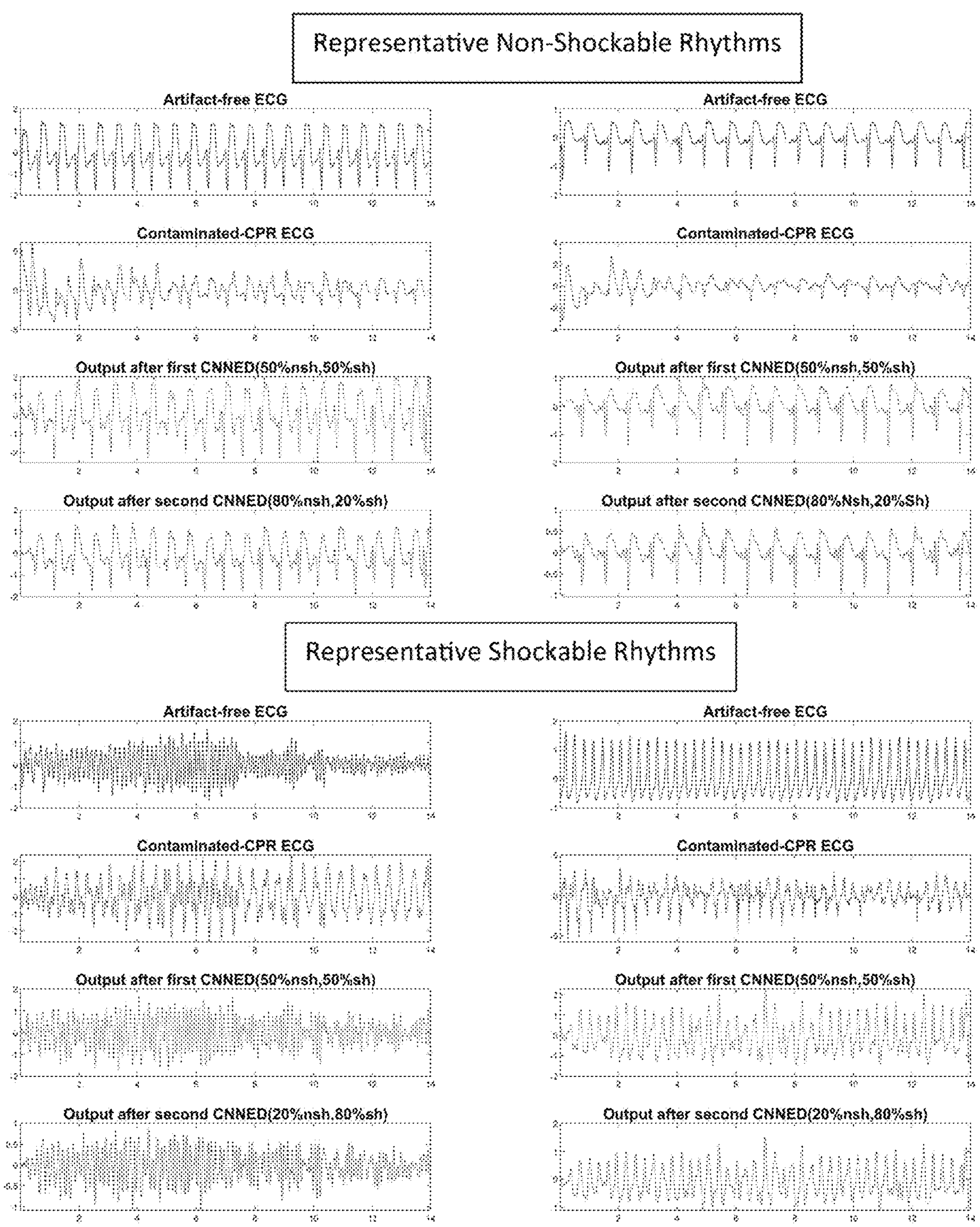
FIG. 12 depicts aspects of filtering results of applying a cascade of CNNEDs on two non-shockable rhythms and two shockable rhythms.

FIG. 12 displays representative ECG signals as they passed through the disclosed procedures. The top four rows show two representative non-shockable rhythms and the bottom four rows show two representative shockable rhythms. The first row for each set of non-shockable and shockable rhythms shows the clean ECG signal, then the second row shows the signal after addition of CPR artifacts. The third row shows the output of the first CNNED pass, while the fourth row shows the final de-noised outcome of using the cascade of CNNED (outlined in the flowchart of FIG. 10). As shown, the novel approach performed well in removing CPR artifacts for both shockable and non-shockable rhythms; the CPR artifact-removed signals have morphologies similar to the clean ECG signals.

As described further above, the first CNNED was designed to remove dominant CPR artifacts, while the second CNNED was intended to make minor adjustments to the dynamics of the remaining signal. Whether these minor adjustments altered the decision-making process of the classifiers via the first use of CNNED, which included balanced shockable and non-shockable training data, and if so, that segment was labeled as indeterminate.

To assess the performance of the disclosed imbalanced training data scheme as well as to determine its optimal data split, three different scenarios were examined. In particular, 70% and 30% training data segmentations were examined each for both shockable and non-shockable data, 80% and 20%, and 90% and 10%. As shown in Table 1, the second row provided the highest accuracy and the fewest inconclusive decisions. This row was trained using 80% non-shockable and 20% shockable data, and conversely, another CNNED was trained using 80% shockable and 20% non-shockable data. All results henceforth will be based on using 80%-20% training data split for both non-shockable and shockable rhythms.

The performance of the cascade of CNNED structure with imbalanced trained data for the second use of CNNED (last column) was compared to the general CNNED model trained using equal amounts of shockable and non-shockable data portions (4th column), which are shown in Table 2. As shown in Table 2, a marked improvement is seen especially in the sensitivity of shockable classification, albeit all categories have improved. Note the greater than 5% increase in sensitivity for shockable classification with the novel specific CNNED model when compared to the general CNNED model (using only one classification and trained using only balanced data). The overall (both shockable and non-shockable results combined) accuracy, sensitivity, and specificity values are 97.3%, 98.2%, and 92.2%, respectively (not shown in table). Hence, the results show the validity of the novel model that in cases where either residual CPR artifacts are present, or dynamics of arrhythmias are similar between shockable and non-shockable, more accurate shock classification can be made with the procedures outlined in FIG. 10.

Tables 3 and 5 show how many of the test data segments had changed classification decisions from the first use of CNNED to the second use of CNNED for non-shockable rhythms. Tables 4 and 6 show the same classification decisions for shockable rhythms. The indeterminate decision, as shown in these tables, amounted to only 8.5% (317 out of 3744) of the shockable data and only 2.5% (522 out of 20,384) of the non-shockable data in the study.

Note that the arrhythmia classification algorithm is not perfect even for a clean ECG signal without CPR artifact. It is shown in Table 7 the results of the novel cascade CNNED approach followed by an arrhythmia classification algorithm used in an FDA approved AED applied to clean ECG signals. The purpose of this computation is to show that the novel trained cascade CNNED structure does not alter dynamics of clean ECG such that arrhythmia classifications retain their accuracies. The results of the novel cascade CNNED approach (see Table 2) for shockable rhythms after removing CPR artifacts (95% for course VF and 88% for rapid VT) are rather impressive when compared to the clean shockable ECG signals. The results of the novel cascade CNNED approach (see Table 2) for non-shockable rhythms after removing CPR artifacts is even more impressive as they are nearly identical to the clean non-shockable ECG signals.

TABLE 3

| Rhythm | Distribution of Specific Rhythms within Their Respective Groups |
|---|---|
| NSR | 35 out of 8788 (0.4%) |
| AFib | 52 out of 1716 (3%) |
| Asystole | 0 out of 468 (0%) |
| SB | 2 out of 416 (0.4%) |
| PVC | 31 out of 1924 (1.6%) |
| AFL | 15 out of 676 (2.2%) |
| SVT | 129 out of 2444 (5.2%) |
| RSVT | 88 out of 1092 (8%) |
| Other Non-Shockable | 34 out of 2860 (1%) |
| Total | 386 out of 20,384 (1.9%) |

The number of classification decisions changed from non-shockable to shockable from the first CNNED to the second CNNED. Although the true rhythm classification is non-shockable, these segments are considered indeterminate.

TABLE 4

| Rhythm | Distribution of Specific Rhythms within Their Respective Groups |
|---|---|
| Course VF | 110 out of 2132 (5.1%) |
| Rapid VT | 112 out of 1612 (7%) |
| Total | 212 out of 3744 (5.6%) |

The number of classification decisions changed from non-shockable to shockable from the first CNNED to the second CNNED. Although the true rhythm classification is shockable, these segments are considered indeterminate.

TABLE 5

| Rhythm | Distribution of Specific Rhythms within Their Respective Groups |
|---|---|
| NSR | 24 out of 8788 (0.27%) |
| AFib | 26 out of 1716 (1.5%) |
| Asystole | 12 out of 466 (2.5%) |

TABLE 5-continued

| Rhythm | Distribution of Specific Rhythms within Their Respective Groups |
|---|---|
| SB | 10 out of 416 (2.4%) |
| PVC | 18 out of 1924 (0.94%) |
| AFL | 2 out of 676 (0.3%) |
| SVT | 24 out of 2444 (1%) |
| RSVT | 1 out of 1092 (0%) |
| Other Non-shockable | 19 out of 2860 (0.6%) |
| Total | 136 out of 20,384 (0.67%) |

The number of classification decisions changed from shockable to non-shockable from the first CNNED to the second CNNED. Note that the true rhythm classification is non-shockable but these segments are considered indeterminate.

TABLE 6

| Rhythm | Distribution of Specific Rhythms within Their Respective Groups |
|---|---|
| Course VF | 48 out of 2132 (2.2%) |
| Rapid VT | 57 out of 1612 (3.5%) |
| Total | 105 out of 3744 (2.8%) |

The number of classification decisions changed from shockable to non-shockable from the first CNNED to the second CNNED. Note that the true rhythm classification is shockable but these segments are considered indeterminate.

TABLE 7

The performance on clean ECG data in the absence of CPR.

| Clean ECG rhythm | Arrhythmia Classification Performance |
|---|---|
| Course VF | 98.55% Sensitivity |
| Rapid VT | 90.91% Sensitivity |
| NSR | 100% Specificity |
| AF, SB, SVT, RSVT, PVC | 99.55% Specificity |

CPR plays an important role in treating out-of-hospital cardia arrest (OHCA). However, the mechanical pressure applied during CPR can lead to significant motion artifacts in the electrocardiogram (ECG) morphology. These artifacts make it challenging to accurately determine whether defibrillation is necessary or not without stopping the CPR maneuver.

Disclosed is a novel structure having a cascade use of CNNED denoising blocks to remove CPR artifacts, along with a new decision-making concept. The novel structure and associated method improves the reliability of decision-making processes related to defibrillation. Ultimately, the novel structure and associated method provides a reliable CPR artifact removal technique so that shockable versus non-shockable decisions can be made without CPR stoppage in near real-time. The clinical impact of the disclosure is that the current practice of requiring CPR for a two-minute period followed by a pause to determine the shock versus no shock decision with AEDs can be disrupted. Hence, with the disclosed cascaded CNNED approach near real-time shock analysis is possible thus eliminating the conventional CPR pause and providing flexible timing of the defibrillatory shock, thereby significantly reducing the required conventional two-minute CPR period with current AEDs to potentially improve outcomes.

It is difficult to determine if the classification outcome is the true desired output. This uncertainty raises concerns about the reliability of the denoising process and subsequent decision-making. Having a second decision process using the disclosed imbalanced training data in the second use of CNNED provides additional assurance of the decision-making process with the novel disclosed approach.

Secondly, certain non-shockable rhythms, such as SVT and rapid SVT, have frequency dynamics and morphology that are close to shockable rhythms like rapid ventricular tachycardia. Better discrimination capabilities for these types of rhythms using the novel cascade CNNED approach have been shown when compared to the conventional methods.

Hence, the novel disclosed approach improves the reliability of the denoising process. Specifically, improved reliability is achieved by noting the change of the arrhythmia classification outcomes between the first and the second use of CNNED. For example, a decision is considered as inconclusive if a change between the first and the second decisions is observed. This is justified for the following reason: when a rhythm is classified as shockable after the first use of CNNED but changed to non-shockable after the second use of CNNED, this raises a question of reliability. Since the second CNNED was trained using 80% shockable and 20% non-shockable data, this network is inherently designed to favor shockable decisions. The same reasoning applies to CNNED trained with 80% non-shockable and 20% shockable. Given that the second CNNED is specifically designed to favor either shockable or non-shockable, when a classification decision changes from the first use of CNNED, this outcome is questionable. Indeed, these outcomes have been observed and delegating them to indeterminate led to better results, especially for shockable rhythms. By flagging indeterminate cases, potentially incorrect decisions that could have unwanted consequences for patients are prevented. This aspect of the disclosed approach ensures a more cautious and accurate decision-making process.

Figure 13:
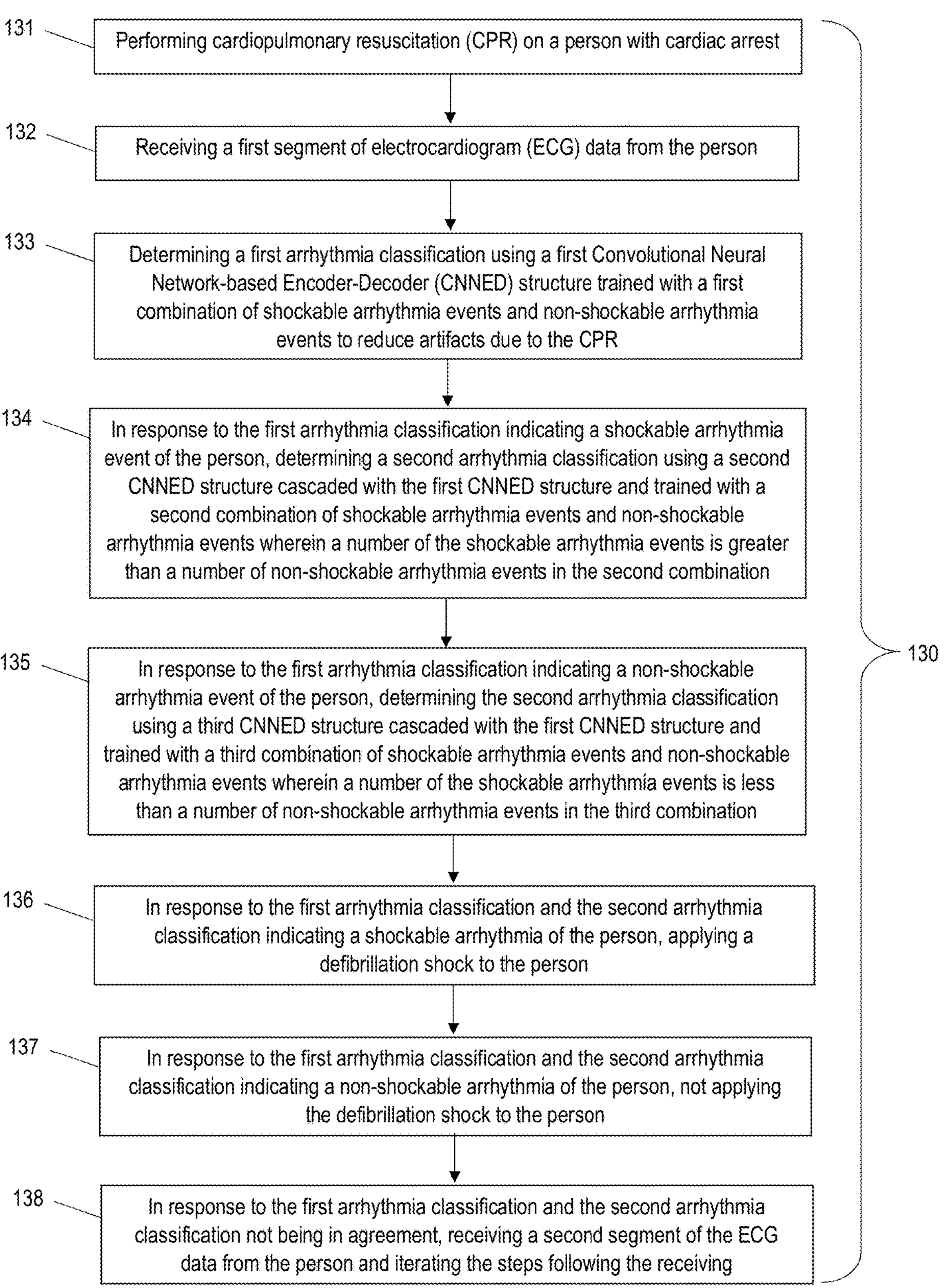
FIG. 13 is a flowchart for a method for treating a person with cardiac arrest.

FIG. 13 illustrates a flowchart for a method 130 for treating a person with cardiac arrest. Step 131 calls for performing cardiopulmonary resuscitation (CPR) on the person. Step 132 calls for receiving a first segment of electrocardiogram (ECG) data from the person. Step 133 calls for determining a first arrhythmia classification using a first Convolutional Neural Network-based Encoder-Decoder (CNNED) structure trained with a first combination of shockable arrhythmia events and non-shockable arrhythmia events to reduce artifacts due to the CPR. Step 134 calls for in response to the first arrhythmia classification indicating a shockable arrhythmia event of the person, determining a second arrhythmia classification using a second CNNED structure cascaded with the first CNNED structure and trained with a second combination of shockable arrhythmia events and non-shockable arrhythmia events wherein a number of the shockable arrhythmia events is greater than a number of non-shockable arrhythmia events in the second combination. Step 135 calls for in response to the first arrhythmia classification indicating a non-shockable arrhythmia event of the person, determining the second arrhythmia classification using a third CNNED structure cascaded with the first CNNED structure and trained with a third combination of shockable arrhythmia events and non-shockable arrhythmia events wherein a number of the shockable arrhythmia events is less than a number of non-shockable arrhythmia events in the third combination. Step 136 calls for in response to the first arrhythmia classification and the second arrhythmia classification indicating a shockable arrhythmia of the person, applying a defibrillation shock to the person. Step 137 calls for in response to the first arrhythmia classification and the second arrhythmia classification indicating a non-shockable arrhythmia of the person, not applying the defibrillation shock to the person. Block 138 calls for (in response to the first arrhythmia classification and the second arrhythmia classification not being in agreement) receiving a second segment of the ECG data from the person and iterating the steps following the receiving.

The method 130 may also include in response to the first arrhythmia classification and the second arrhythmia classification not being in agreement for a selected number of segments of the ECG data, stopping the CPR for a selected time period, receiving a post-CPR segment of the ECG data, restarting the CPR, and iterating the actions following the receiving.

In one or more embodiments, the defibrillation shock is applied by an automated external defibrillator.

In one or more embodiments, the first combination of shockable arrhythmia events and non-shockable arrhythmia events includes a number of shockable arrhythmia events being approximately equal (e.g., within 5%) to a number of non-shockable events.

In one or more embodiments, the second combination of shockable arrhythmia events and non-shockable arrhythmia events includes approximately (e.g., within 5%) 80% shockable arrhythmia events and 20% non-shockable arrhythmia events.

In one or more embodiments, the third combination of shockable arrhythmia events and non-shockable arrhythmia events includes approximately (e.g., within 5%) 20% shockable arrhythmia events and 80% non-shockable arrhythmia events.

In one or more embodiments, the CNNED structure includes an input layer, a plurality of convolution layers, a plurality of deconvolution layers, a regression layer, and an output layer. In one of more embodiments, the CNNED structure may include one or more skip connections. In one or more embodiments, the one or more skip connections may connect a convolution layer to a deconvolution layer.

Figure 14:
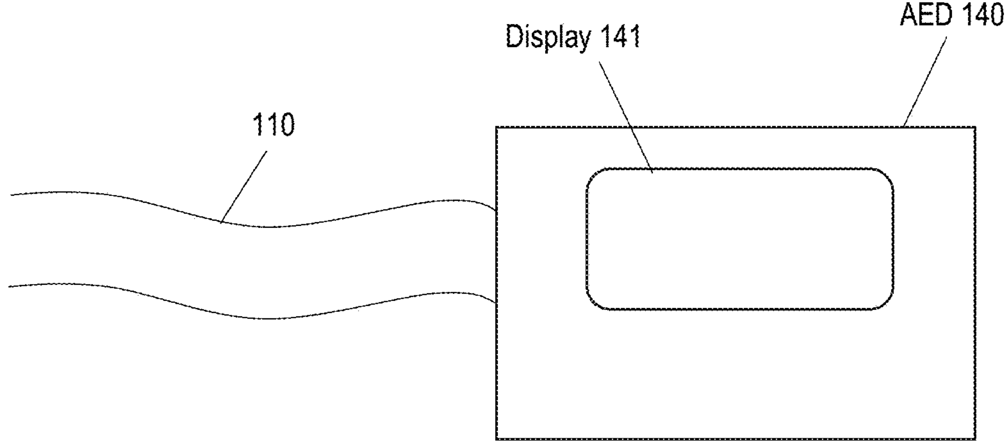
FIG. 14 depicts aspects of an automated external defibrillator (AED).

FIG. 14 illustrates an embodiment of an AED 140. The AED 140 includes leads 110 extending from an enclosure of the AED 140. The AED 140 also includes a display 141 in or on the enclosure. The display 141 is coupled to the processor 202 and is configured to display operational aspects of the AED 140. For example, the display 141 may be configured to display a first indication that a defibrillation shock will not be applied to the person that is experiencing cardiac arrest. In another example, the display 141 may be configured to display a second indication informing that the CPR should be temporarily stopped for a selected period of time to obtain a clean segment of ECG data. In some embodiments, the AED 140 is automated or semi-automated, and at least partially initiates a defibrillation shock therapy as an output of the analyses described herein.

The CNNED structure trained and implemented in such a new and different way are beyond what is achievable by pen and paper or prior techniques, removing or reducing the time-consuming and laborious—and quite often inaccurate—behavior of manual analysis. Further, techniques described herein are not those previously used in a manual process. These specific techniques, as described herein, for training and application of the CNNED structure are an improvement in technology or technical field related to administering a defibrillation shock. As shown in FIGS. 11 and 12, the techniques described herein at least improve the administration of a defibrillation shock by ensuring that the type of fibrillation occurring is a person undergoing cardiac arrest requires the defibrillation shock for treatment. Further, the techniques described herein do not pre-empt every method of improving treatment or monopolize the basic tools of scientific or technological work.

Generally, as discussed herein, the term "shockable" refers to medical condition of a patient or subject where initiation of an electrical shock is or has been determined likely to be of therapeutic benefit to the patient. Conversely, "non-shockable" generally refers to medical condition of a patient or subject where initiation of an electrical shock is or has been determined likely to be detrimental to the health or therapy of the patient or subject. As used herein, the terms "shockable" and "non-shockable" may be used as modifiers describing qualities of aspects such as sinus rhythm and arrhythmia.

Generally, as discussed herein, the term "CNNED block" refers to steps in a logic process (for example, see FIGS. 10 and 11). That is, the term "CNNED block" is not meant to be construed as prevention of a therapeutic process or analysis. Rather, CNNEDs blocks, as discussed herein, present logic steps where data classification, data manipulation (for example, "denoising" or removal of artifacts) and other similar steps are performed.

Generally, as discussed herein, the term "denoising" and variations thereof, refer to removal or reduction of CPR artifacts from cardiac data. That is, as discussed herein, CPR induced noise can appear in cardiac data, thus confounding the data and complicating clinical analyses. Denoising is a process whereby at least a portion of the CPR and/or other systemic noise is removed or reduced from the cardiac data such that improvements in data classification and clinical assessments may be realized. Adequacy of denoising may be best determined by practitioners and/or clinical outcomes.

All statements herein reciting principles, aspects, and embodiments of the disclosure, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure.

Various other components may be included and called upon for providing for aspects of the teachings herein. For example, additional materials, combinations of materials and/or omission of materials may be used to provide for added embodiments that are within the scope of the teachings herein. Adequacy of any particular element for practice of the teachings herein is to be judged from the perspective of a designer, manufacturer, seller, user, system operator or other similarly interested party, and such limitations are to be perceived according to the standards of the interested party.

In the disclosure hereof any element expressed as a means for performing a specified function is intended to encompass any way of performing that function including, for example, a) a combination of circuit elements and associated hardware which perform that function or b) software in any form, including, therefore, firmware, microcode or the like as set forth herein, combined with appropriate circuitry for executing that software to perform the function. Applicants thus regard any means which can provide those functionalities as equivalent to those shown herein. No functional language used in claims appended herein is to be construed as invoking 35 U.S.C. § 112 (f) interpretations as "means-plusfunction" language unless specifically expressed as such by use of the words "means for" or "steps for" within the respective claim.

When introducing elements of the present invention or the embodiment(s) thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements. The term "exemplary" is not intended to be construed as a superlative example but merely one of many possible examples.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered with only a true scope and spirit being indicated by the following claims.

What is claimed is:

1. An apparatus for treating a person having cardiac arrest, the apparatus comprising:

a processor;

a lead in communication with the processor, wherein the lead is configured to receive a first segment of electrocardiogram (ECG) data from the person when the person is undergoing cardiopulmonary resuscitation (CPR); and a non-transitory computer-readable medium comprising:

a first Convolutional Neural Network-based Encoder-Decoder (CNNED) structure to reduce artifacts due to the CPR;

a second CNNED structure cascaded with the first CNNED structure to further reduce artifacts due to the CPR;

first instructions operable upon execution by the processor to (i) determine a first arrhythmia classification using the first CNNED structure, (ii) determine a second arrhythmia classification using the second CNNED structure in response to the first arrhythmia classification indicating a shockable arrhythmia event of the person; and (iii) transmit a signal to apply a defibrillation shock to the person in response to the first arrhythmia classification and the second arrhythmia classification indicating a shockable arrhythmia of the person.

2. The apparatus according to claim 1, wherein the first CNNED structure is trained with a first combination of shockable arrhythmia events and non-shockable arrhythmia events and the second CNNED structure is trained with a second combination of shockable arrhythmia events and non-shockable arrhythmia events wherein a number of the shockable arrhythmia events is greater than a number of non-shockable arrhythmia events in the second combination.

3. The apparatus according to claim 2, wherein the non-transitory computer-readable medium further comprises:

a third CNNED structure cascaded with the first CNNED structure and trained with a third combination of shockable arrhythmia events and non-shockable arrhythmia events wherein a number of the shockable arrhythmia events is less than a number of non-shockable arrhythmia events in the third combination to further reduce artifacts due to the CPR; and second instructions operable upon execution by the processor to (iv) determine the second arrhythmia classification using the third CNNED structure in response to the first arrhythmia classification indicating a non-shockable arrhythmia event of the person; and (v) not apply the defibrillation shock to the person in response to the first arrhythmia classification and the second arrhythmia classification indicating a non-shockable arrhythmia of the person.

4. The apparatus according to claim 3, wherein the non-transitory computer-readable medium further comprises third instructions operable upon execution by the processor to receive a second segment of the ECG data from the lead and implement the first instructions and the second instructions using the second segment in response to the first arrhythmia classification and the second arrhythmia classification not being in agreement.

5. The apparatus according to claim 4, wherein the non-transitory computer-readable medium further comprises fourth instructions operable upon execution by the processor to stop the CPR for a selected time period, receive a post-CPR segment of the ECG data, restart the CPR, and implement the first instructions and the second instructions using the post-CPR segment in response to the first arrhythmia classification and the second arrhythmia classification not being in agreement for a selected number of segments of the ECG data.

6. The apparatus according to claim 2, wherein the first combination of shockable arrhythmia events and non-shockable arrhythmia events includes a number of shockable arrhythmia events being approximately equal to a number of non-shockable events.

7. The apparatus according to claim 6, wherein the second combination of shockable arrhythmia events and non-shockable arrhythmia events includes approximately 80% shockable arrhythmia events and 20% non-shockable arrhythmia events.

8. The apparatus according to claim 7, wherein the third combination of shockable arrhythmia events and non-shockable arrhythmia events includes approximately 20% shockable arrhythmia events and 80% non-shockable arrhythmia events.

9. The apparatus according to claim 2, wherein at least one of the first CNNED structure, the second CNNED structure, or the third CNNED structure comprises an input layer, a plurality of convolution layers, a plurality of deconvolution layers, a regression layer, and an output layer.

10. A non-transitory computer-readable medium associated with treating a person having cardiac arrest comprising:

instructions operable upon execution by a processor to receive a first segment of electrocardiogram (ECG) data from the person when the person is undergoing cardiopulmonary resuscitation (CPR);

a first Convolutional Neural Network-based Encoder-Decoder (CNNED) structure trained with a first combination of shockable arrhythmia events and non-shockable arrhythmia events to reduce artifacts due to the CPR;

a second CNNED structure cascaded with the first CNNED structure and trained with a second combination of shockable arrhythmia events and non-shockable arrhythmia events wherein a number of the shockable arrhythmia events is greater than a number of non-shockable arrhythmia events in the second combination to further reduce artifacts due to the CPR; instructions operable upon execution by the processor to determine a first arrhythmia classification using the first CNNED structure, determine a second arrhythmia classification using the second CNNED structure in response to the first arrhythmia classification indicating a shockable arrhythmia event of the person; and instructions operable upon execution by the processor to transmit a signal to apply a defibrillation shock to the person in response to the first arrhythmia classification and the second arrhythmia classification indicating a shockable arrhythmia of the person.

11. The non-transitory computer-readable medium according to claim 10, further comprising:

a third CNNED structure cascaded with the first CNNED structure and trained with a third combination of shockable arrhythmia events and non-shockable arrhythmia events wherein a number of the shockable arrhythmia events is less than a number of non-shockable arrhythmia events in the third combination to further reduce artifacts due to the CPR; and instructions operable upon execution by the processor to: determine the second arrhythmia classification using the third CNNED structure in response to the first arrhythmia classification indicating a non-shockable arrhythmia event of the person; and not apply the defibrillation shock to the person in response to the first arrhythmia classification and the second arrhythmia classification indicating a non-shockable arrhythmia of the person.

12. The non-transitory computer-readable medium according to claim 11, further comprising instructions operable upon execution by the processor to receive a second segment of the ECG data from the lead and implement the instructions using the second segment in response to the first arrhythmia classification and the second arrhythmia classification not being in agreement.

13. The non-transitory computer-readable medium according to claim 11, further comprising instructions operable upon execution by the processor to transmit a signal to indicate stopping the CPR for a selected time period, receive a post-CPR segment of the ECG data, restart the CPR, and implement the instructions using the post-CPR segment in response to the first arrhythmia classification and the second arrhythmia classification not being in agreement for a selected number of segments of the ECG data.

14. The non-transitory computer-readable medium according to claim 11, wherein the first combination of shockable arrhythmia events and non-shockable arrhythmia events includes a number of shockable arrhythmia events being approximately equal to a number of non-shockable events.

15. The non-transitory computer-readable medium according to claim 14, wherein the second combination of shockable arrhythmia events and non-shockable arrhythmia events includes approximately 80% shockable arrhythmia events and 20% non-shockable arrhythmia events.

16. The non-transitory computer-readable medium according to claim 15, wherein the third combination of shockable arrhythmia events and non-shockable arrhythmia events includes approximately 20% shockable arrhythmia events and 80% non-shockable arrhythmia events.

17. The non-transitory computer-readable medium according to claim 11, wherein at least one of the first CNNED structure, the second CNNED structure, or the third CNNED structure comprises an input layer, a plurality of convolution layers, a plurality of deconvolution layers, a regression layer, and an output layer.

18. The non-transitory computer-readable medium according to claim 17, wherein at least one of the first CNNED structure, the second CNNED structure, or the third CNNED structure comprises a skip connection connecting a convolution layer in the plurality of convolution layers to a deconvolution layer in the plurality of deconvolution layers.

19. The non-transitory computer-readable medium according to claim 17, wherein at least one of the first CNNED structure, the second CNNED structure, or the third CNNED structure comprises a skip connection connecting one layer in the plurality of convolution layers to another layer in the plurality of convolution layers, two layers being separated by one or more in-between layers.

20. An automated external defibrillator comprising:

a processor;

a lead associated with the processor, wherein the lead is configured to receive a first segment of electrocardiogram (ECG) data from a person when the person is undergoing cardiopulmonary resuscitation (CPR); and a non-transitory computer-readable medium comprising machine executable instructions for implementing a method comprising:

a first Convolutional Neural Network-based Encoder-Decoder (CNNED) structure trained with a first combination of shockable arrhythmia events and non-shockable arrhythmia events to reduce artifacts due to the CPR;

a second CNNED structure cascaded with the first CNNED structure and trained with a second combination of shockable arrhythmia events and non-shockable arrhythmia events wherein a number of the shockable arrhythmia events is greater than a number of non-shockable arrhythmia events in the second combination to further reduce artifacts due to the CPR;

a third CNNED structure cascaded with the first CNNED structure and trained with a third combination of shockable arrhythmia events and non-shockable arrhythmia events wherein a number of the shockable arrhythmia events is less than a number of non-shockable arrhythmia events in the third combination to further reduce artifacts due to the CPR;

first instructions operable upon execution by the processor to (i) determine a first arrhythmia classification using the first CNNED structure, (ii) determine a second arrhythmia classification using the second CNNED structure in response to the first arrhythmia classification indicating a shockable arrhythmia event of the person; and (iii) apply a defibrillation shock to the person in response to the first arrhythmia classification and the second arrhythmia classification indicating a shockable arrhythmia of the person;

second instructions operable upon execution by the processor to (iv) determine the second arrhythmia classification using the third CNNED structure in response to the first arrhythmia classification indicating a non-shockable arrhythmia event of the person; and (v) not apply the defibrillation shock to the person in response to the first arrhythmia classification and the second arrhythmia classification indicating a non-shockable arrhythmia of the person;

third instructions operable upon execution by the processor to receive a second segment of the ECG data from the lead and implement the first instructions and the second instructions using the second segment in response to the first arrhythmia classification and the second arrhythmia classification not being in agreement; and fourth instructions operable upon execution by the processor to stop the CPR for a selected time period, receive a post-CPR segment of the ECG data, restart the CPR, and implement the first instructions and the second instructions using the post-CPR segment in response to the first arrhythmia classification and the second arrhythmia classification not being in agreement for a selected number of segments of the ECG data;

a shock application device coupled to the lead and to the processor and configured to apply the defibrillation shock through the lead to the person in response to receiving a signal from the processor to apply the shock; and a display coupled to the processor and configured to display a first indication that a defibrillation shock will not be applied to the person and a second indication informing that the CPR should be temporarily stopped for a selected period of time to obtain a clean segment of ECG data in response to a signal received from the processor.

* * * * *